US009663794B2

(12) United States Patent
Tu et al.

(10) Patent No.: US 9,663,794 B2
(45) Date of Patent: May 30, 2017

(54) HEAT-RESISTANCE RICE GENE OSZFP, SCREENING MARKER AND SEPARATION METHOD THEREOF

(71) Applicants: ZHEJIANG UNIVERSITY, Hangzhou, Zhejiang Province (CN); RICE RESEARCH INSTITUTE, GUANGDONG ACADEMY OF AGRICULTURAL SCIENCES, Guangzhou, Guangdong Province (CN)

(72) Inventors: Jumin Tu, Hangzhou (CN); Xuhua Zhong, Guangzhou (CN); Jianping Liu, Hangzhou (CN); Nongrong Huang, Guangzhou (CN)

(73) Assignees: Zhejiang University, Hangzhou, Zhejiang Province (CN); Rice Research Institute, Guangdong Academy of Agricultural Sciences, Guangzhou, Guangdong Province (CN)

( * ) Notice: Subject to any disclaimer, the term of this patent is extended or adjusted under 35 U.S.C. 154(b) by 0 days.

(21) Appl. No.: 14/730,622

(22) Filed: Jun. 4, 2015

(65) Prior Publication Data
US 2015/0267219 A1    Sep. 24, 2015

Related U.S. Application Data

(63) Continuation-in-part of application No. PCT/CN2013/001504, filed on Dec. 5, 2013.

(30) Foreign Application Priority Data

Dec. 5, 2012 (CN) .......................... 2012 1 0515449

(51) Int. Cl.
| | | |
|---|---|---|
| C12N 15/82 | (2006.01) |
| C07K 14/415 | (2006.01) |
| A01H 1/04 | (2006.01) |
| A01H 5/10 | (2006.01) |
| C12Q 1/68 | (2006.01) |

(52) U.S. Cl.
CPC .......... *C12N 15/8271* (2013.01); *A01H 1/04* (2013.01); *A01H 5/10* (2013.01); *C07K 14/415* (2013.01); *C12Q 1/6876* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

2008/0148432 A1* 6/2008 Abad ................... C07K 14/415
800/279

FOREIGN PATENT DOCUMENTS

CN         102433334 A     5/2012
WO    WO 2009/029771 A2    3/2009

OTHER PUBLICATIONS

Huang et al 2008 Gene 420:135-144.*
Wu et al 2011 Theor Appl Genet 122:915-923.*
Baker et al. "Growth and yield responses of rice to carbon dioxide concentration", *J. Agric. Sci.* 115(03):313-320 (1990).
Carriger et al. "More Crop per Drop", *Asia Biotech* 12(6):22-25 (2008).
Maggs et al. "Growth and yield responses of Pakistan rice (*Oryza sativa* L.) cultivars to $O_3$ and $NO_2$", *Environmental Pollution* 103:159-170 (1998).
Yoshida "Fundamentals of Rice Crop Science", *The International Rice Research Institute* (1981) Book.
GenBank Accession No. NM_001069405 (2010) URL: http//www.ncbi.nlm.nih.gov/nucleotide/115478552.
GenBank Accession No. NP_001062870 (2010) URL: http://www.ncbi.nlm.nih.gov/protein/115478553.
Wei "Evaluation Procedure Establishment and Gene Mapping of Rice High Temperature Resistance at Seedling Stage: A dissertation submitted to Zhejiang University for the requirements of the degree of Doctor of Crop science" *Agricultural Sciences* No. 8, pp. D047-D115 (2013).
Wei et al. "A Dominant Major Locus in Chromosome 9 of Rice (*Orzasativa* L.) Confers Tolerance to 48° C. High Temperature at Seedling Stage", *J. Heredity* 104(2):287-294 (2012).
International Search Report corresponding to International Application No. PCT/CN2013/001504 mailed Mar. 13, 2014.
International Preliminary Report on Patentability corresponding to International Application No. PCT/CN2013/001504 mailed Jun. 9, 2015.
Written Opinion of the International Searching Authority corresponding to International Application No. PCT/CN2013/001504 mailed Mar. 13, 2014.

\* cited by examiner

*Primary Examiner* — Brent Page
(74) *Attorney, Agent, or Firm* — Myers Bigel, P.A.

(57) ABSTRACT

Provided in the present invention are a separated endogenous rice gene resistant to high temperature (hereinafter referred to as the OsZFP gene for short) and a polypeptide encoded thereby, optimizing rice cells comprising the heat-resistant gene of the present invention or the polypeptide encoded thereby, and the plant cell preparation method thereof. Further provided are new methods and technologies for breeding new varieties of heat-resistant crops, comprising the related regulatory sequence for heat-resistance and a closely linked molecular marker denoting the heat-resistant gene and the sequence thereof.

13 Claims, 6 Drawing Sheets

0h  1h  2h  4h  6h  8h  10h  12h

```
                        Znf gene sequence.txt
Oryza sativa L ssp. indica Znf gene sequences:
LOC_Os09g15430 sequence information
Genomic sequence length: 4784 nucleotides
CDS length: 1245 nucleotides
Protein legth: 414 amino acids
Putative function: zinc finger family protein, putative, expressed
_____
Genomic Sequence
>13109. t01339
GAGAAGCGCCACAGGAAAACGAGCCGCGTCGCTTTCGCGAGAGAGGGACACCTGCTCTGC
TTCCGCTTCCGCTTCCCCCTCTCGAGTCTCTCGCCTCTCCCCGTGGCCAACCCACACAC
CGCGGGTTGGAGGAGGAGGAGGAGGAGGTAGGGGAAATCCCCGTCGGCCGTCGGCTCGGC
GCCGAATCGATCCGGTGAGTGAGTGATTGAGTTCGTCTCTGCTCTCTCTCCTCCTTGTTC
AATTATCAAGCTCTTGAATCGAGTCCTAGTAGTAGTGTGCTAGAGGTGCTGGATGATTTG
GGTTTTTGGGGATTTTTTTTTTGGGGGGGGGGGTTGTTTGGGAACTGCTAGTGCGTTT
GTGGTATACTGGTATGGGAGTTCGTTGCTAATGGACGGGGTATTTGGGAACTTTTAGGGT
TTTGTTTGGATGGATTTTTGGTTGTGGTTTTTGTCAGGAATGGGTGTCGGCGACTTGGTT
AGCTTTAGCTTTTGAGAATTTTTTTCGCCCCTGTTGTTCTGTTCATGGTTCATCTTTAGA
TTCAGAGGAGAATCCTTCTAGCGTTTTTCTGAGAATGAAACCTTTTTTTTTATGTTTTTA
TTTTTACGGGGCTATAATTTTTCCACTGCCTTTTGTGATTACTATTACATAATTACATGT
CCCTTTGATGAATAATGGATGTTGGTTCTTTGGCTAAAAGTCAAATTGCGACTTGAAGTA
GAAACGGGTGTACCTGGGATTAAGTTGCCATCGCTGGAACTAGAGTTAATTATTGGTTTG
ATCATTGTTGCTTCGCGTTGGATATACTATCGGTTTAGCAGTTAGCATGATACTAAATCA
TAGGAAGGCTACTATGATTGGAGAACCGTGGTGTTGTATAACTGATTAGATTCTTTCAAA
TATGATTTTCAGTTAGACCGCTCATTGGTTCAGGATCAGGGTCTTTTGCAGTTCTCCCAA
ATATTGCACTAATTTGTTTGCCAAATAATCATGCAAAACTTACATGAGTGGTGGCATTAA
CTCTTTTATTCAAATACATGGTTGTTCAATGATGGTATTAACTCTTCTATTCAACAGGCT
GTAAAAAATTAAGTGAATAATCCTTGTCCCGCTACTTAAAATCTAGTCAAGACTCAGATT
GGAAACCATTGGGGACTAGTAAAGTTTATGGGACTTGGACGTGTACATTACATGCACATG
CCCATGATACATTAACAGGATGGATGTTCTATTCTGGAAGGTTAAATATAATAGTTCTTA
GAAAGTTAGAGTTTTCAGACCGATGGTATGCTTGCATATATTTTTAGAAGTATCAAATAT
GATGAGAGTTCTTAAAAGAATTGGGTTTGTTAACTATGTTGAGTGCCTTCTACTATTTAT
TTTACAGGTTTTTATTGTTCATGGTGATATACTATATGCATGAATAAGTTACAGTTATGT
AATATATATGGGCAAGGATGTATAAGAAGTTCATTTGTTTTCTAAATTTGTAGCTTAGGC
TTCTTCTGCTGGGCTCTTCCATGAAGCAAATGAAGTTTATAATGCACATACTAATGTTCA
GTATATTATACTGAGAATCAACTTTATTCTCAGCTGTATATACACTAGTATGCCAGCCAT
TGGTAGCTACTTGAAAGGATGGTGAAACGCATATGATTACCCATGATGAGCATGTGTGTT
CCCTTTTTTTATTAGTGCTAAGCTGGAAATCAATAAATCCAAGATATTCATGGAGCATGC
TACCTGTGATGATGTGCATGAGCATGCTATAAATGTATCACATGGAGAAACTGCATCAAC
ATCAACCAGTCATCAAGATTTGCACAGTGATTCAGATGATTCACATCAGGATGATAGGCC
TTCAACAAGCACACAAACCCCATCACCACAGTCTTCAGCATCAACTTCGCCCACTGCATA
TAACACCAGAAATTTATCCTTTCCTAGAAGAGATAGTATGTATGGTCATGGAAGAAGTAT
TTGGAATTCTGGTTTGTGGATCTCGTTTGAACTGGTCATATATGTAGTACAGATTGTAGC
TGCTATTTTCGTCCTTGTCTTTTCAAGAGACGAACATCCGCATGCCCCTTTATTTGCATG
GATAATTGGTTACACAATTGGCTGCATTGCAAGCATTCCTCTTATTTGTTGGCGCTGTGC
CCATCGAAACAGACCTTCGGAACAAGAACCTGAACAACCACCCGCAGCCTATCCTAATTT
GACTTCCTCTCAATCATCAGAAGGACGCAATCAGCGTAGCAGTGGTACTGTTTTGCATTT
TGGATGTATCACAATTTCGTGTCCAAGGTAATTTGTAGTTCCATGTTATTTTTCTATCTT
GAATTTCCTAAAGTCCTGTATGTGAACTCGTGTATGCAGTCTCACTCCTATGCATTTTTT
GAAGAAACTGCTATCCATTTGCATCTTATAAACATATTTATGCTTTCCAATAACTGAAAG
ATGCAACAAATAAACTGATAGTTGAATTGATTGAAACTATCAACTCTAGGGCATCCTAAT
TAGTTTATTTTTGATATTCCATTGGATCACGCAGGTACCACAGTCCTATGTTCTTGAGTT
GAGCCTTCTATTTGTGCGTAGTACCACGATATGGATTCTACAATATATTTTTACTGCAAT
```

Fig. 8

TTGTTTTTTCTCAGTCATTCTGGAAGTGTAGAAGATATATATGCTCTTGTTTCTTTGACC
TAGGAATTTGGAACAGTTGTGTTGACCTCTTCAAGGTGTAATATTACAATGTTCGCTGCA
GATACCTCATTACATTGGAGGGGAGGATGTTCCCTTTCTATATTTGTTGTGCTTGACAAA
AGCATTCAACATTGTGGAGCGTAATGTGTCCTATTTAACTGGAATTGGTCCTGTTGAAAA
TTGTACTAGTCTACTCTAAAGTATTAAAACTTTATAAGTAAATTTGAAGAAATGCGTGAT
GCGAGATCTTATAGTACTTAGTTTTGTGCTAAATTTGATATGGATGTATTAACTGAGGTG
ATTATACATTACAGGCCTAGCATATTGGCTTATCATTTCAAGACAGCTGTAGACTGTTTC
TTTGCTGTATGGTTTGTTGTTGGCAATGTGTGGATTTTTGGTGGGCACAGCACTTTGTCA
GATTCTCAGGAAGCTCCCAATATGTATAGGTATTTTCTTTCCTATCATTCATAGCTTTTC
TGAACTCAATCAACTCATGCCTTACTTTGTTGCCTCTTGCTAGGCTATGCTTAGCATTCC
TTGCACTTAGTTGTGTTGGGTATGCTATTCCCTTCGTCATGTGTGCAGCCATATGCTGCT
GCTTTCCATGCTTAATTTCTCTTCTGCGCCTTCAAGAGGATTTGGGTCATACTAGAGGAG
CTACTCAAGAACTAATTGATGCACTGCCAACCTACAAATTCAAGCCAAAACGAAGCAAAA
TGTGGGTTGACCATGCTTCAAGCTCAGAGAATCTTAGCGAGGGTGGCATCCTGGGCCCAG
GAACTAAAAAGGAAAGGATTGTTTCAGCTGAAGATGCTGTGAGTATATTTCACATTTTCA
TATCATTTTCATGTCTGATGATACTTGATTTGCAATTAGTATTGAGGGGGTTTCCGTAAA
ACAAGTATTGATGGGATTCCTTGTATCGACCTTCATGTACCTTATAATTTAGTAATCATA
ACTCCATTCACAAGTGAATACTTAAGCAGCCTCTGTTATGCAGTAATATGTACTGTCTTA
GCCTTATCTTATTTTGGAATATATTTAACAAAAGGTCTAGCTCGTGATGATGCTTTTACA
CATCTTTTTCAGATAACAATGAGACTTCCCTTTTTTCCTCAGTGAAACATATAGTGTTCT
AGGTAAATATTCATTAACAAAAGTGTTTTAGGGAAATATTCTGCTTTATGAGAAATAGTT
TTGTTTATATTATACTACAGTATCTTTTTTCTCGTGTATCTTCAAACAGTTGTAGTTACA
CTCGCTTTCATAAGTCCTTTTCTAAATTCCATTCATTTCCTTCAGTAACATGGGACCTCT
TGGAATTTTCCAAGTTACCTGACTTACTGTCTGGATTATTATTTTTGTAGCTCATTCAAT
TTGCCATTACTAACTTGAAACCAGGGTTCTCGAAATAATGTTATAGTTGTTTTAGTTTGA
TTCATAAGTCATAACATATAACTTGTCAACATCTATTGATATCTGCAGGTGTGCTGCATC
TGTCTTACTAAGTACGGAGATGATGATGAGCTCCGTGAGCTTCCTTGCACCCACTTCTTT
CATGTGCAATGTGTCGATAAATGGCTCAAGATAAATGCAGTGTGCCCACTCTGCAAGACC
GAGATTGGGGGTGTGGTTCGATCATTTTTTGGCTTGCCCTTTGGTCGCCGACGTGTTGAT
AGGATGGCAGGAAGAGGTATAGCTAGCTCGAGATTCACTGTATAGAACACGTCTTCTTCT
CTAGCATGTTTGCTTGTTTCATCTGCTCATATGCACATAAAAGACGTGCTCATGGATTGT
AGTTTGTTGATTTGCAATGAAAGCGATAATCTGCTTTCATCACCCTTGAGTTCACCAAAG
TGATGACAGAAAAGTGGAGACCTGATGCTTGCAGTGACAAGTTTCTGCAGTACAGTAGAA
ACATAAGTATATTCTGATGTAACATTTGATGTCAAGATTGTAAATAAAGAGCACAAAGTT
CACTTCGGGGGTGTATATCTGCATGTGTATGGGAAAGGAAAGCCTAATTAGTTAGTAACT
TTGTGGGCATTTTATTGTGTGCAATCATTGATCTTGTTTTTCCC (SEQ ID NO:1)

---

CDS
>13109. m01458
ATGGAGCATGCTACCTGTGATGATGTGCATGAGCATGCTATAAATGTATCACATGGAGAA
ACTGCATCAACATCAACCAGTCATCAAGATTTGCACAGTGATTCAGATGATTCACATCAG
GATGATAGGCCTTCAACAAGCACACAAACCCCATCACCACAGTCTTCAGCATCAACTTCG
CCCACTGCATATAACACCAGAAATTTATCCTTTCCTAGAAGAGATAGTATGTATGGTCAT
GGAAGAAGTATTTGGAATTCTGGTTTGTGGATCTCGTTTGAACTGGTCATATATGTAGTA
CAGATTGTAGCTGCTATTTTCGTCCTTGTCTTTTCAAGAGACGAACATCCGCATGCCCCT
TTATTTGCATGGATAATTGGTTACACAATTGGCTGCATTGCAAGCATTCCTCTTATTTGT
TGGCGCTGTGCCCATCGAAACAGACCTTCGGAACAAGAACCTGAACAACCACCCGCAGCC
TATCCTAATTTGACTTCCTCTCAATCATCAGAAGGACGCAATCAGCGTAGCAGTGGTACT
GTTTTGCATTTTGGATGTATCACAATTTCGTGTCCAAGGCCTAGCATATTGGCTTATCAT
TTCAAGACAGCTGTAGACTGTTTCTTTGCTGTATGGTTTGTTGTTGGCAATGTGTGGATT
TTTGGTGGGCACAGCACTTTGTCAGATTCTCAGGAAGCTCCCAATATGTATAGGCTATGC
TTAGCATTCCTTGCACTTAGTTGTGTTGGGTATGCTATTCCCTTCGTCATGTGTGCAGCC
ATATGCTGCTGCTTTCCATGCTTAATTTCTCTTCTGCGCCTTCAAGAGGATTTGGGTCAT
ACTAGAGGAGCTACTCAAGAACTAATTGATGCACTGCCAACCTACAAATTCAAGCCAAAA

Fig. 8 (cont'd.)

```
CGAAGCAAAATGTGGGTTGACCATGCTTCAAGCTCAGAGAATCTTAGCGAGGGTGGCATC
CTGGGCCCAGGAACTAAAAAGGAAAGGATTGTTTCAGCTGAAGATGCTGTGTGCTGCATC
TGTCTTACTAAGTACGGAGATGATGATGAGCTCCGTGAGCTTCCTTGCACCCACTTCTTT
CATGTGCAATGTGTCGATAAATGGCTCAAGATAAATGCAGTGTGCCCACTCTGCAAGACC
GAGATTGGGGGTGTGGTTCGATCATTTTTTGGCTTGCCCTTTGGTCGCCGACGTGTTGAT
AGGATGGCAGGAAGAGGTATAGCTAGCTCGAGATTCACTGTATAG (SEQ ID NO:2)
```

```
Protein
>13109. m01458
MEHATCDDVHEHAINVSHGETASTSTSHQDLHSDSDDSHQDDRPSTSTQTPSPQSSASTS
PTAYNTRNLSFPRRDSMYGHGRSIWNSGLWISFELVIYVVQIVAAIFVLVFSRDEHPHAP
LFAWIIGYTIGCIASIPLICWRCAHRNRPSEQEPEQPPAAYPNLTSSQSSEGRNQRSSGT
VLHFGCITISCPRPSILAYHFKTAVDCFFAVWFVVGNVWIFGGHSTLSDSQEAPNMYRLC
LAFLALSCVGYAIPFVMCAAICCCFPCLISLLRLQEDLGHTRGATQELIDALPTYKFKPK
RSKMWVDHASSSENLSEGGILGPGTKKERIVSAEDAVCCICLTKYGDDDELRELPCTHFF
HVQCVDKWLKINAVCPLCKTEIGGVVRSFFGLPFGRRRVDRMAGRGIASSRFTV*
(SEQ ID NO:3)
```

HEAT-RESISTANCE RICE GENE OSZFP, SCREENING MARKER AND SEPARATION METHOD THEREOF

RELATED APPLICATIONS

This application is a continuation-in-part of International Patent Application No. PCT/CN2013/001504 filed Dec. 5, 2013 which claims priority to Chinese Application No. 201210515449.2 filed Dec. 5, 2012, the entire content of each of which is incorporated herein by reference in its entirety.

STATEMENT REGARDING ELECTRONIC FILING OF A SEQUENCE LISTING

A Sequence Listing in ASCII text format, submitted under 37 C.F.R. §1.821, entitled 9363-21TSIPv2_ST25.txt, 18,333 bytes in size, generated on Sep. 25, 2015 and filed via EFS-Web, is provided in lieu of a paper copy. The Sequence Listing is incorporated herein by reference into the specification for its disclosures.

TECHNICAL FIELD

The present invention relates to the field of plant genetic engineering and molecular breeding technology. More particularly, the present invention relates to mapping, isolation, functional analysis, sequence characterization of heat tolerance genes, identification of regulatory sequences, as well as screening and creation of co-segregating molecular markers, and their uses for improving the stress resistance of crops such as rice, and genetic transformation of a heat tolerance gene into rice and molecular marker-assisted method and procedure for selection. The invention further relates to use of the heat tolerance gene in assistance of improving the stress resistance of rice and other crops.

BACKGROUND ART

Rice is the most important food crop, and is the main source of food for more than half of the population all over the world (Khush, 2005). It is reported that an annual increase rate of 0.6 to 0.9% in rice yield is needed to meet the needs of people's lives (Carriger and Vallee, 2007). The increase of crop yield depends on farmland, and the sustainable development of agricultural production requires avoidance of environmental deterioration, destruction of ecological balance and loss of biodiversity (Cassman, 1999; Tilman et al., 2002). Crop yield is mainly determined by photosynthesis and respiration, however, both photosynthesis and respiration are sensitive to temperature (Yoshida, 1981), and also influenced by $CO_2$ concentration in the atmosphere (Baker et al., 1990) and ozone layer (Maggs and Ashmore, 1998). These factors are also related to the greenhouse effect (Rosenzweig and Parry, 1994). Continual climate warming has brought devastating impacts on rice production. For two consecutive years 2006 and 2007, high temperature weather above 38° C. occurred for a long term in a large area along the middle and lower Yangtze River, including such as Chongqing, Hubei, Hunan, Anhui, Zhejiang, and Guangdong provinces, leading to large-scale drop of yield of rice and other crops in a large area, with ripening rate lower than 50% in the severe cases. Therefore, there is an urgent need for available heat tolerance genetic resources in breeding to respond to the serious threat of rice production caused by global warming. Therefore, it is of great significance in both theory and practice to carry out an extensive research on high temperature resistance, develop further heat tolerance genetic resource, and make efforts to select and breed new plant varieties with high temperature resistance, so as to respond to the serious threat of rice production caused by global warming.

In recent years, a large number of studies of genetic analysis and chromosomal mapping have been carried out at home and abroad regarding the high temperature resistance at the rice booting stage (Zhigang Zhao et al., 2006), heading stage (Yongsheng Zhang, et al., 2009; Zhang et al., 2009.), flowering stage (Liyong Zhao et al., 2003, 2002; Yi Pan et al., 2005; Qingquan Chen, 2008; Tao Zhang et al., 2008; Limei Que et al., 2008; Zhang et al., 2009; Jagadish et al., 2010.), filling stage (Changlan Zhu et al., 2005) and the stage for rice amylose synthesis and gel consistency formation (Changlan Zhu et al., 2006). In these studies, the mapped rice high temperature resistance related quantitative trait loci (referred to as QTL) relates to each chromosome of rice, wherein the QTL site with the most significant genetic effects is from variety Bala from Pakistan, which is responsible for 18% of phenotypic variation. However, since different researchers use different test materials and different high temperature treatment procedures and methods, the experimental data obtained are difficult to correspond to each other and reproduce, and the mapped QTL interval is relatively large, making it impossible to determine candidate genes and carry out the related molecular cloning and functional complementary verification. Therefore, the above mapped high temperature resistance related QTLs, not only theoretically lack support by the necessary data, but also are difficult to be used in practice effectively.

In addition, some researchers also carried out studies on rice high temperature resistance related genes by homologous cloning methods. Yamanouchi et al., (2002) used map-based cloning method for mapping, and cloned a rice spot gene Sp17. It is found that one of reading frame of the gene is highly similar with heat stress transcription factor. Under conditions of heat stress, the expression amounts of mutant and wild-type Sp17 are both up-regulated. Yokotani et al., (2008) transferred heat resistant gene encoding OsHsfA2e of rice into *Arabidopsis thaliana* and the tolerance of the transgenic *A. thaliana* to environmental stress is enhanced. According to the microarray analysis on transgenic *A. thaliana* plant with over-expression under non-stress condition exhibited increased expression amounts of some genes related to stress, including several types of heat shock proteins.

It is generally believed that heat shock proteins (HSPs) are associated with the high temperature response. It has been reported that rHsp90 responds to several stresses such as salt, drought and high temperature, and high temperature treatment at 42° C. and 50° C. for 30 minutes can significantly increase the rHsp90 expression amount (Liu et al., 2006). There is another report showing that there are 40 genes encoding proteins containing α-crystals, 23 of which are heat shock proteins (Sarkar et al., 2009). The microarray and RT-PCR analyses show that the expression amounts of 19 out of 23 heat shock proteins are up-regulated at high temperatures. In addition, Chang et al. (2007) transferred the rice heat shock protein Hsp101 into tobacco, and found that at high temperatures, the survival of the plant with over-expression is better than that of wild-type. Wu et al. (2009) drove OsWRKY11 expression with HSPIO promoter and found that the transgenic rice plants have relatively slower leaf wilting and a high survival rate after heat treatment. By over-expressing rice OsCEST (chloroplast protein capable of enhancing stress resistance) gene in *A. thaliana*, Yokotani et al. (2011) found that the transgenic plant is resistant to not only salt stress, but also is to drought and high temperature.

Zinc finger protein is a large family of transcription factors, which play important roles in gene expression regulation, cell differentiation, embryonic development and other biological processes (Gerisman & Pabo, 1997; Laity et al., 2001), especially in the expression regulation of stress related genes (Li & Chen, 2000). According to the number and location of cysteine (C) and histidine (H) residues in zinc finger protein, the transcription factors containing zinc-finger protein domains can be classified into subclasses C2H2, C2C2, C3H, C3HC4 (i.e., RING finger), C3HC5 (i.e., LM finger) and others. Among them, C2H2 zinc finger proteins are of the most clearly studied class among the zinc finger proteins, wherein two cysteines and two histidines form a coordinate bond with $Zn^{2+}$, thereby forming in turn a tight finger structure containing one β fold and one α-helix. Kim et al. (2001) isolated a cold-inducible zinc finger protein gene SCOF-1 from the soybean cDNA library, which encodes a product containing two typical C2H2 zinc finger structures. The expression of SCOF-1 is specifically induced by cold and ABA, rather than salt stress. The transgenic study confirmed that the over-expression of SCOF-1 can enhance the cold resistance of *A. thaliana* and tobacco. Liu M. et al. (2007) cloned a soybean C2H2 zinc finger protein transcription factor gene GmC2H2, whose expression is related with the stress induction of cold and ABA. As for C3HC4 and CHY zinc finger proteins, the successful isolation are only reported in *A. thaliana*, rice, *Physcomitrella patens, Artemisia desertorum*, corn, pineapple, soybeans and other plants (Stone et al., 2005; Ohyanagi et al., 2006; Rensing et al., 2008; Yang et al., 2008; Alexandrov et al., 2009; Yang X. et al., 2009; Wu X. et al., 2010). *A. desertorum* AdZFP1 gene is a typical example that encodes such zinc finger proteins (Yang et al. 2008), and the semi-quantitative PCR analysis showed that, AdZFP1 gene is strongly induced by exogenous ABA, and to some extent is also induced by high salt, low temperature and high temperature. Wu X. et al. (2010) also screened a C3HC4 zinc finger protein gene GmRZFP1 from the cDNA library of the soybeans under drought condition, and the results demonstrated that the gene is mainly induced by high temperatures and drought stress. During the high temperature stress for 1-6 hours, the expression amount of GmRZFP1 Gene is positively correlated with treatment duration. In particular, under the high-temperature stress for 12 hours, the expression amount decreased, while the expression reached the highest level at 24 hours. These results therefore showed that GmRZFP1 gene is induced by a variety of stress treatments, probably involving in multiple stress signal transduction.

In addition, Huang et al. (2008) found 12 A20/AN1 type zinc finger proteins from the *Japonica*. The microarray analysis showed that the expressions of four genes (ZFP177, ZEP181, ZFP176, ZFP173), two genes (ZFP181 and ZFP176) and one gene (ZFP157) are induced by cold, drought and $H_2O_2$, respectively. Further study shows that ZFP177 responds to both low temperature and high temperature stress. By over-expressing ZFP177 gene, the obtained transgenic tobacco resists to low temperature of 2° C. and high temperature of 55° C., but becomes more sensitive to salt stress and drought stress, suggesting that ZFP177 plays an important role in various abiotic stresses in plant, while different stresses may have different response mechanisms.

REFERENCES

LiYong Cao, Jiangen Zhao, Xiaodeng Zhan, Denglou Li, Libin He, Shihua Cheng. QTL mapping of heat resistance in rice and the correlation between heat resistance and photosynthetic rate. Chinese Rice Science, 2003, 17 (3): 223-227.

LiYong Cao, Jun Zhu, Songtao Zhao. QTLs mapping of heat resistance in *Indica* Rice DH hybrid Population. Journal of Agricultural Biotechnology, 2002, 10 (3): 210-214.

Qingquan Chen, Sibin Yu, Chunhai Li, Tongmin Mou. Mapping analysis of heat resistance related QTL of rice at heading to flowering stage. Chinese Agricultural Sciences, 2008, 41 (2): 315-32.

Limei Kui, Lubin Tan, Jian Tu, Yixuan Lu, Chuanqing Sun. QTL mapping of heat resistance of the wildtype rice at heading to flowering stage in Yuanjiang, Yunnan. Journal of Agricultural Biotechnology, 2008, 16 (3): 461-464.

Mengmeng Liu. Cloning and characterization of soybean C2H2 zinc finger transcription factor protein. Beijing: China Agricultural University, 2007.

Yi Pan, Lihua Luo, and Huabing Deng, Guilian Zhang, Wenbang Tang, Liyun Chen, Yinghui Xiao. QTL mapping of pollen sterility in rice at flowing stage under high temperature stress Chinese Rice Science, 2011, 25 (1): 99-102.

Xuechuang Wu, Xinyou Cao, Ming Chen, Xiaoke Zhang, Yangna Liu, Zhaoshi Xu, Liancheng Li, Youzhi Ma. Cloning and expression analysis of soybean C3HC4 RING zinc finger protein gene GmRZFP1, Plant Genetic Resources, 2010, 11 (3): 343-348.

Xiangyan Yang, Yuanbao Cai, Qingsong Wu, Guangming Sun. Cloning and Expression Analysis of Pineapple Zinc Finger Protein gene AcRCHY1. Horticulture Sinica, 2009, 36 (11): 1589-1596.

Tao Zhang, Li Yang, Kaifeng Jiang, Min Huang, Qun Sun, Wenfu Chen, Jiakui Zheng. QTL analysis of heat resistance in rice at heading and flowering stages. Molecular Plant Breeding, 2008, 6 (5): 867-873.

Yongsheng Zhang, Xi Liu, Ling Jiang, Liangming Chen, Shijia Liu, Huqu Zhai, Jianmin Wan. QTL mapping analysis of Nanjing 11X Yueguang RIL populations at heading stage. Jiangsu Agricultural Sciences, 2009, 2 (1): 6-12.

Zhigang Zhao, Ling Jiang, Yinghui Xiao, Wenwei Zhang, Huqu Zhai. QTLs analysis of heat resistance of rice at booting stage (*Oryza sativa* L.) Crop Sinica, 2006, 32 (5): 640-644.

Changlan Zhu, Ling Jiang, Wenwei Zhang, Chunming Wang, Huqu Zhai, Jianmin Wan. QTL analysis of the effect of rice amylose synthesis and gel consistency formation on high temperature resistance. Chinese Rice Science, 2006, 20 (3): 248-250.

Changlan Zhu, Yinghui Xiao, Chunming Wang, Ling Jiang, Huqu Zhai. Quantitative trait loci analysis of heat resistance of rice at filling stage. Chinese Rice Science, 2005, 19 (2): 117-121.

Alexandrov N N, Broer V V, Freidin S, Troukhan M E, Tatarinova T V, Zhang H, Swaller T J, Lu Y P, Bouck J, Flavell R B, Feldmann K A. (2009) Insights into com genes derived from large-scale cDNA sequencing. Plant Molecular Biology. 69:179-194.

Baker J. T., Allen L. H., J., Boote K. J. (1990) Growth and yield responses of rice to carbon dioxide concentration. J. Agric. Sci. 115, 313-320.

Carriger S., Vallee D. (2007) More crop per drop. Rice Today. 6:10-13.

Cassman, K. G. (1999) Ecological intensification of cereal production systems: Yield potential, soil quality, and precision agriculture. Proc. Natl. Acad. Sci. USA 96: 5952-5959.

Chang C. C., Huang P. S., Lin H. R., Lu C. H. (2007) Transactivation of protein expression by rice HSP101 in planta and using Hsp101 as a selection marker for transformation. Plant Cell Physiol. 48(8):1098-1107.

Gerisman H. A, Pabo C. (1997). A general strategy for selecting high-affinity zinc finger protein for diverse DNA target sites. Science. 275:657-661.

Jagadish S. V. K., Cairnsb J., Lafitte R., Wheeler T. R., Price A. H., Craufurd P. Q. (2010a) Genetic analysis of heat tolerance at anthesis in rice. Crop Science. 50(5):1633-1641.

Khush G. S. (2005) What it will take to feed 5.0 billion rice consumers in 2030. Plant Mol Biol. 59: 1-6.

Kim J. C., Lee S. H., Cheong Y. H., Yoo C. M., Lee S. I., Chun H. J., Yun D. Y., Hong J. C., Lee S. Y., Lim C. Q., Cho M. J. (2001) A novel cold-inducible zinc finger protein from soybean, SCOF-1, enhances cold tolerance in transgenic plants. The Plant Journal. 25(3):247-259.

Liu D., Zhang X., Cheng Y., Takano T., Liu S. (2006) rHsp90O gene expression in response to several environmental stresses in rice (Oryza sativa L.). Plant Physiol Biochem. 44: 380-386.

Maggs, R., Ashmore, M. R. (1998) Growth and yield responses of Pakistan rice (Oryza sativa L.) cultivars to $O_3$ and $NO_2$. Environmental Pollution. 103: 159-170.

Ohyanagi H., Tanaka T., Sakai H., Shigemoto Y., Yamaguchi K., Habara T., Fujii Y., Antonio B A., Nagamura Y., Imanishi T., Ikeo K., Rensing S. A., Zimmer A. D., Terry A., Salamov A., Salamov A., Shapiro H., Nishiyama T., Perroud P. F., Lindquist E. A., Kamisugi Y., Tanahashi T. (2008) The physomitrella genome reveals evolutionary insights into the conquest of land by plants. Science. 319(5859):64-69.

Rosenzweig C., Parry M. L. (1994) Potential impact of climate change on world food supply. Nature. 367: 133-138.

Sarkar N. K., Kim Y. K., Grover A. (2009) Rice sHsp genes: genomics organization and expression profiling under stress and development. BMC Genomics. 10:1-18.

Stone S L., Hauksadottir H., Troy A., Herschleb J., Kraft E., Callis J. (2005) Functional analysis of the RING-type ubiquitin ligase family of Arabidopsis. Plant Physiology. 137(1):13-30.

Tilman D., Cassman K. G., Matson P. A., Naylor, R., Polasky S. (2002) Agricultural sustainability and intensive production practices. Nature 418, 671-677.

Wu X. L., Yoko S., Sachie K., Yukihiro I., Kinya T. (2009) Enhanced heat and drought tolerance in transgenic rice seedlings overexpressing OsWRKY11 under the control of HSP101 promoter. Plant Cell Rep. 28: 21-30.

Yamanouchi U., Yano M., Lin H., Ashikari M., Yamada K. (2002) A rice spotted leaf gene, Spl7, encodes a heat stress transcription factor protein. PNAS. 99(11): 7530-7535.

Yang X. H., Sun C., Hu Y. L., Lin Z. P. (2008). Molecular cloning and characterization of a gene encoding RING zinc finger ankyrin protein from drought-tolerant Artemisia desertorum, Journal of Biosciences. 33(1):103-112.

Yokotani N., Higuchi M., Kondou Y., Ichikawa T., Iwabuchi M., Hirochika H., Matsui M., Oda K. (2011) A novel chloroplast protein, CEST induces tolerance to multiple environmental stresses and reduces photooxidative damage in transgenic Arabidopsis. Journal of Experimental Botany. 62(2):557-569.

Yokotani N., Ichikawa T., Kondou Y., Matsui M., Hirochika H., Iwabuchi M., Oda K. (2008) Expression of rice heat stress transcription factor OsHsfA2e enhances tolerance to environmental stresses in transgenic Arabidopsis. Planta, 227:957-967.

Yoshida S. (1981) Fundamentals of Rice Crop Science (International Rice Research Institute, Los Banos, Philippines). pp 69-83.

Zhang G. L., Chen L. Y., Xiao G. Y., Xiao Y. H., Chen X. B., Zhang S. T. (2009) Bulked segregant analysis to detect QTL related to heat tolerance in rice (Oryza sativa L.) using SSR markers. Agricultural Sciences in China. 8(4): 482-487.

SUMMARY OF THE INVENTION

To solve the above problems, through the intensive studies, the present inventors have developed an optimized method for mapping the stress-resistance gene in plants, especially the high temperature-resistant gene, provided a number of new markers for genetic screening and mapping, and precisely mapped a new high temperature-resistant gene in rice, thereby providing a breeding method for converting a temperature-sensitive plant to a non-temperature-sensitive plant, and converting an ordinary plant to a plant with resistance to high temperature. In particular, the present invention relates to the following aspects:

1. A polypeptide, selected from any one of the following:
A) a polypeptide comprising an amino acid sequence as shown in SEQ ID NO:3;
B) a polypeptide comprising an amino acid sequence derived from the amino acid sequence as shown in SEQ ID NO:3 by deleting, substituting or inserting one or more amino acids; and having a function of providing high temperature resistance;
C) a polypeptide having an amino acid sequence as shown in SEQ ID NO:3; and
D) a polypeptide of an amino acid sequence as shown in SEQ ID NO:3.

2. A gene, wherein the polynucleotide sequence of the gene is a polynucleotide sequence selected from any one of the following:
A) a polynucleotide comprising a nucleotide sequence as shown in SEQ ID NO:1;
B) a polynucleotide comprising a polynucleotide sequence obtained by keeping the nucleotides corresponding to those at positions 2360 to 2371 of the nucleotide sequence as shown in SEQ ID NO:1 unchanged as GGGGGGGGGGGG (SEQ ID NO:12), and subjecting one or more nucleotides at the other positions of the nucleotide sequence to deletion, addition, or insertion; and encoding a polypeptide having a function of providing high temperature resistance;
C) a polynucleotide having a nucleotide sequence as shown in SEQ ID NO:1;
D) a polynucleotide of a nucleotide sequence as shown in SEQ ID NO:1; and
E) a polynucleotide sequence encoding any one of the polypeptide according to item 1.

3. A vector comprising the gene of item 2.

4. A host cell, characterized in that said cell comprises the polypeptide according to item 1, or the gene according to item 2, or the vector according to item 3, wherein the host cell is preferably an eukaryotic cell, more preferably a plant cell and a yeast cell, the plant cell is preferably a Gramineae plant cell, particularly preferably a rice (Oryza sativa L.) cell.

5. A molecular marker for screening, mapping and isolating new nucleotide sequences, wherein the marker is selected from:
A) insertion/deletion marker InDel5, located between 9130-9150 kb from the short arm terminus on chromosome 9 of rice, and the amplification product of the marker has a length polymorphism;
B) SNP marker, referred as RBsp1407, corresponding to the sequences of TGT705ACA and TGG705ACA in high temperature sensitive and high temperature resistant rice plants, respectively, based on the polynucleotide sequence of SEQ ID NO:1;
C) Microsatellite DNA marker RM7364, located between 9440-9450 kb from the short arm terminus on chromosome 9 of rice, and the amplification product via primers of the marker has a length polymorphism.
6. Use of the marker of item 5 for screening, mapping and isolating high temperature sensitive/resistive genes, wherein the high temperature is preferably 42° C. or higher, 45° C. or higher, 48° C. or higher, or 50° C. or higher.
7. A method of plant breeding, said method comprising applying the polypeptide according to item 1, or applying the gene according to item 2, or the vector according to item 3, or the host cell according to item 4, or the marker according to item 5 or 6.
8. A method of converting a temperature-sensitive rice to a non-temperature-sensitive rice, the method comprising mutating the nucleotide corresponding to the nucleotide at position 705 of SEQ ID NO:1 on chromosome 9 of the genome of the rice with the temperature-sensitive phenotype to G by genetic manipulation.
9. A method of inducing a high temperature resistant phenotype in rice, the method comprising inserting G at the 5' end of the position corresponding to position 2360 of SEQ ID NO:1 on chromosome 9 of the genome of the rice without the temperature-resistant phenotype by genetic manipulation, wherein the high temperature is preferably 42° C. or higher, 45° C. or higher, 48° C. or higher, or 50° C. or higher.
10. A method of converting a temperature-sensitive rice to a high-temperature resistant rice, the method comprising mutating, by genetic manipulation, the nucleotide corresponding to the nucleotide at position 705 of SEQ ID NO:1 on chromosome 9 of the genome of the rice with the temperature-sensitive phenotype to G, and inserting one G at upstream from the 5' end of the position 2360 in chromosome 9 of the genome of the temperature-sensitive rice, so as to obtain a nucleotide sequence being the same as the nucleotides from positions 2360 to 2371 in SEQ ID NO:1, i.e., the sequence comprises 12 continuous Gs from position 2360 in the direction away from the start codon, wherein the high temperature is preferably 42° C. or higher, 45° C. or higher, 48° C. or higher, or 50° C. or higher.
11. The present invention relates to a method of identification of high temperature resistance in plants, the method can be summarized as follows: subjecting a soil-cultivated seedling at two-leaf stage to a three-leaf stage to a high temperature treatment at 45-48° C. for 79 h, observing the results of the temperature responses after recovery for 5 days; as a standard procedure for the identification of high temperature resistance, the relative humidity and other cultivation conditions are set on the same level.
12. The method according to item 11, preferably further comprising using a pot for each cultivation with a uniform size (length 43 cm; width 33 cm; height 10 cm), weighing and adding the same amount of potting soil with a cultivation scale of 5×12 seedlings/each variety with one line of high temperature material positioned around as a protective line to eliminate the marginal effect, leaving a clear boundary between the protective line and the formal experimental materials; during the treatment, the humidity in the growth chamber is set at 75%, and length of light/dark cycle is set at 12 h.

BRIEF DESCRIPTION OF DRAWINGS

FIG. 8 The DNA sequence (SEQ ID NO:1), encoding sequence (SEQ ID NO:2) and the amino acid sequence (SEQ ID NO:3) of its expression product of the heat tolerance gene OsZFP according to the present invention.

DETAILED DESCRIPTION OF THE INVENTION

Figure 1:
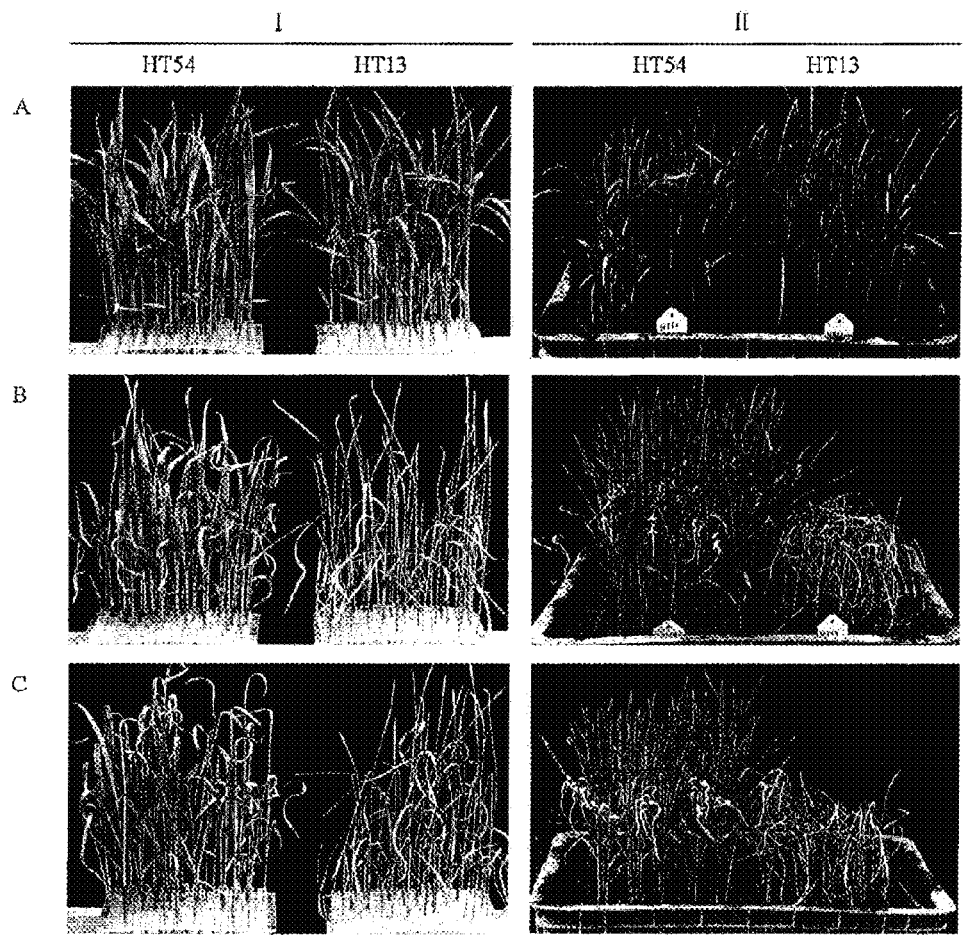
FIG. 1 High temperature stress treatment assay and the response of the high temperature resistant and sensitive varieties HT54 and HT13 to the high temperature stress. Shown in FIG. 1 is growth status of the soil-cultivated seedlings at two-leaf stage, which has been subjected to different high temperature treatments for 79 hours and recovered for 5 days. Panel A: high temperature treatment at 42° C.; Panel B: high temperature treatment at 45° C.; Panel C: high temperature treatment at 48° C. It can be seen from the photographed results that the high temperature resistant variety HT54 and the high temperature sensitive variety HT13 exhibit a substantive difference in terms of survival and death after high temperature treatments at 45° C. and 48° C.

To solve the above problems, the inventors have made intensive studies and achieved the present invention on the basis of a large number of test results. The present invention will be described in detail in combination with the accompanying drawings.

I. Standardized Procedure for Identifying High Temperature Resistance of Rice at Seedling Stage First, the inventors establish a standardized procedure of for identifying high temperature resistance of rice at seedling stage. The outstanding advantages of this identification procedure are clear typing of high temperature resistant and sensitive varieties, good reproducibility, and excellent applicability. Therefore, the establishment of the procedure will provide a good technical basis for screening, evaluating high temperature resistant rice germplasm material, genetic analysis of heat tolerance genes, and chromosomal mapping and cloning. See Example 1 for details of the identification.

II. Molecular Mapping of Rice Heat Tolerance Genes

Based on the above test results, the inventors use high temperature resistant rice line HT54, high temperature sensitive rice line HT13 and the progeny hybrids F1 and F2 thereof as exemplary test materials to perform molecular mapping of rice heat tolerance gene.

Test Method (1). Screening of Polymorphism Markers in Parents

The molecular mapping of rice heat tolerance gene is performed with microsatellite DNA length polymorphism markers (SSLP) with high polymorphism and good reproducibility. The SSR primers used are based on the primer sequences published in the Gramene database and the NCBI database and synthesized by Shanghai Sangon Service Company.

Rice genome DNA extraction is performed according to the small amount of DNA extraction method reported by McCouch et al. (1988). Specifically, the method comprises the following steps: 1) A small piece of leaf with a length of 4-5 cm is sampled, added with 700 µL 1.5×CTAB (containing 1.5% CTAB, 75 mM Tris-HCl, 15 mM EDTA, 1.05 M NaCl), and thoroughly ground; 2) the homogenate is transferred into a 1.5 ml centrifuge tube, incubated in a water bath at 56° C. for 20 min and cooled to room temperature; 3) an equal volume of chloroform: isoamyl alcohol (24:1) is added and shaken till uniform; 4) the sample is centrifuged at maximum speed (13200 rpm) for 10 min; 5) the supernatant is transferred to a new centrifuge tube, and added with two volumes of ice-cold 100% ethanol, stands for 20 min followed by collection of DNA by centrifugation; 6) the supernatant is discarded and the DNA is air-dried, added with 50-100 µL double-distilled water, and detected in UV spectrophotometer. A series of DNA working solution with concentration ranging from 50-100 ng/µL is prepared by diluting the DNA based on the determined concentration, and stored at 4° C. refrigerator for further uses.

2) Construction of Mapping Populations

In autumn of 2008, a hybrid F1 was prepared with the high temperature resistant material HT54 as male parent and the high temperature sensitive material HT13 as female parent in the experimental base of the Institute of Rice, Guangdong Academy of Agricultural Sciences. The female parent HT13 is treated via "warm-both emasculation" approach. Considering that HT13 is a temperature sensitive material, the temperature of the both is set at 2° C. lower than the normal case in order to avoid damage to the pistil thereof. Specifically: in the heading stage of rice, at around 7:30 am in sunny morning, a panicle of the female parent HT13 (⅔ is taken out) is selected, placed into a water bottle preset at 43° C. for 8 min (the bottle is sealed with cotton after the placement), then taken out and shaken off water droplets. The spikelets (have been pollinated or will bloom in a few days) which are not blooming, should all be removed and the rest are immediately coated in a paper bag. At around 9:00 am, panicles of the male parent HT54 are taken and inserted in a bottle containing tap water, and covered with a black cloth. One hour later, most florets of the male parent are in full bloom. The pollen is transferred to the blooming stigma of the female parent which has experienced high-temperature emasculation. The pollination is repeated for 2-3 times. Once the pollination is completed, the stigma of the female parent is coated with a brown paper bag, which is then clamped with a clip, which is kept away from the stigma. The paper bag is marked with a card, which recites the name and hybridization date. About eight days later, the paper bag is removed and the F1 seeds are harvested when it is ripe.

In the winter of 2008, the hybrid F1 is planted in Hainan province. Once the plants grow up, the leaves are taken for DNA extraction. 3-4 pairs of SSR markers with polymorphism in the two parents are used to determine whether the plant is a true hybrid, and after the plant heading, F2 seeds harvested after self-hybridization of F1 are used for the subsequent identification of high temperature resistance. The genetic analysis of a heat tolerance gene is performed with resistance/sensitivity ratio after high temperature treatment and then the heat tolerance genes are mapped.

3) High Temperature Treatment Procedure

The high temperature treatment of the parents, F1 or F2 is performed following the above seedling cultivation method and standardized high temperature treatment procedure. The specific steps are: a. nursery pots preparation, that is, each nursery pot (size 43 cm×33 cm×10 cm) is added with equal amount of sieved and well mixed paddy soil; b. sowing, that is, the germinated seeds are spaced sowed at 11 rows×18 seeds/pot. Meanwhile, the parents are sowed at 1 row/pot as a control with 2 rows positioned around as protective rows. Fertilizer and water managements are same as those of the rice in pot; C. sampling, that is, once the seedling grows up to three-leaf stage, a piece with a length of about 2-3 cm from the second leaf per plant is placed −80° C. refrigerator for subsequent DNA extraction of the identified sensitive plants. D. After two days of recovery, i.e., one day before the complete growth of the third leaf, the seedling is transferred into the artificial climate chamber for high temperature treatment. The artificial climate chamber is set as follows: 33° C. 1 h (Light, abbreviated as L, the same below)→36° C. 1 h (L)→39° C. 1 h (L)→42° C. 1 h (L)→45° C. 1 h (L)→48° C. 7 h (L)→48° C. 12 h (Dark, abbreviated as D, the same below)→48° C. 12 h (L)→48° C. 12 h (D)→48° C. 12 h (L)→48° C. 12 h (D)→48° C. 12 h (L). Humidity is set at 75%.

(4). PCR Program and Detection

SSR analysis is mainly revised by reference to the method of Wu et al. (1993) with a PCR system of 25 μL: 2.5 μL 10× buffer ($Mg^{2+}$); 0.5 μl 10 mM dNTP; 1.0 μl 5 μM 5'-primer; 1.0 μl 5 μM 3'-primer; 0.5 μl Taq polymerase; 1.0 μl DNA; 18.5 μl dd$H_2$O. dNTP is purchased from Shanghai Sangon Company, and Taq polymerase is purchased from Dingguo Company. PCR amplification program is: denaturation 94° C. for 5 min, then 35 cycles of (denaturation at 94° C. for 45 s, annealing at a temperature of 50-60° C. suitable for the selected primers for 45 s, extension at 72° C. for 45 s), followed by extension at 72° C. for 10 min. The amplification product is detected with 3% agarose gel electrophoresis (AGE) or 4% denaturing polyacrylamide gel electrophoresis (PAGE).

(5) Preliminary Mapping of the Heat Tolerance Gene

F2 segregating population is selected to establish a mapping population for gene mapping using a recessive extreme population method with microsatellite DNA polymorphism molecular marker (also called simple sequence length polymorphism, SSLP) as molecular marker. The specific procedure is as follows: the F2 segregating population is subjected to high temperature treatment, and the selected individual plant exhibiting high temperature sensitivity is used as a mapping population for gene mapping. Then, from the F2 segregating population, 10 high temperature resistant or sensitive plants are randomly selected. Their leaves are mixed in equal amount and grinded for DNA extraction to establish heat tolerance and sensitivity DNA pools. Thereafter, the two DNA pools are subjected to marker analysis using SSLP markers with polymorphism between the parents (Chen et al., 1997; Temnykh et al., 2000) to screen out the marker with polymorphism between the two DNA pools, whereby, the linkage group of the gene is preliminarily identified. On this basis, the mapping population established on the recessive extreme individuals in the above F2 segregating generation is subjected to genotype analysis individually using the polymorphism marker obtained in the DNA pools, and the obtained data is used for preliminary mapping of target genes.

(6) Fine Mapping of Heat Tolerance Gene

On the basis of preliminary mapping, the mapped segment is further analyzed with concentrated markers, until such markers are exhausted on the linkage group related to target gene. The SSLP markers used is either obtained from Gramineae genome database, or designed and synthesized in house according to the genomic sequence. Then, the biological function prediction and molecular characterization (including motifs, functional domains, conserved sequences and control sequences, etc.) analysis are performed on the coding sequence within the marker interval (usually at least less than or equal to 0.5 Mb) with biological information, in order to determine the candidate genes. Then, specific primers are designed for the candidate genes, and the candidate genes are cloned by TA cloning and sequenced. Finally, the target gene is predicted depending on the presence or absence of the difference.

(7) Calculation of Genetic Distance

The results of the electrophoresis images are converted with numerical statistics: those consistent with HT54 banding pattern are marked as A, those consistent with HT13 banding pattern are marked as B, those with the banding pattern of both parents are marked as H, and those with no banding are marked as -.

Genetic linkage analysis is performed using MAP-MAKER3.0 software (Lander et al., 1987) for analysis and calculation of genetic distance (cM), genetic mapping with Mapdraw2.1 (Renhu Liu and Jinling Meng, 2003) and mapping analysis of heat tolerance genes.

For precise mapping of the genes, the inventors have developed a new mapping marker. The exemplary preparation of the marker is shown in Example 2.

The results of genetic analysis and gene mapping

1) Screening of Parental Polymorphism and Establishment of Molecular Map

Figure 6:
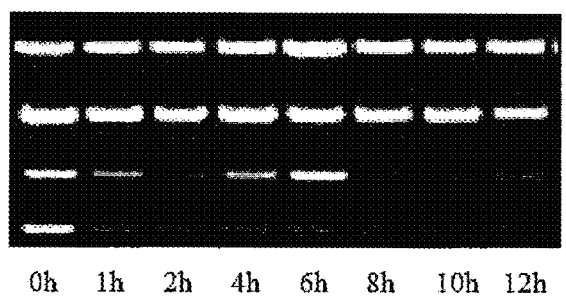
FIG. 6 The dynamic expression pattern analysis of high temperature resistant and sensitive ZFP alleles in response to 45° C. high temperature stress treatment. The analytical method used is real-time quantitative PCR analysis with rice actin gene acts as an internal standard in a PCR amplification of 25 cycles. In the figure, the four rows from top to bottom are HT54 (resistant)/actin, HT13 (sensitive)/actin, HT54 (resistant)/ZFP, HT13 (sensitive)/ZFP, respectively. It can be seen from the figure that the expression levels of ZFP in the 6 h-treated high-temperature resistance and sensitive samples are up-regulated and down-regulated, respectively.

The parents are screened for polymorphism using a total of 2304 SSLP molecular markers, from which 322 SSLP molecular markers with polymorphism between the parents are selected. The distribution of these markers on chromosome is shown in FIG. 6 in the scale of physical distance. The obtained polymorphism SSLP markers are relatively uniformly distributed in each chromosome, besides chromosome 9 and the region near the centromere.

Figure 2:
FIG. 2 The response of the high temperature resistant and sensitive varieties HT54 and HT13 to the high temperature stress. The treatment temperature is 48° C. The duration of the treatment is 84 hours. The treatment is performed at two-leaf stage. The seedlings are cultured in water. The figure shows the survival statues following a recovery period of five days after the treatments.

The microsatellite molecular markers (SSLP) genetic linkage map established by rice heat tolerance gene mapping is shown in FIG. 2. The distance between the markers is physical distance.

2) Genetic Analysis Confirmed that the High Temperature Resistance of HT54 Seedling is Controlled by Major Dominant Single Gene The parents, F1 and F2 hybrids at two-leaf stage are subjected to high temperature treatment using standardized procedure. It is shown that: F1 plants completely survive high temperature treatment, and F2 population exhibits significant segregation into high temperature resistance and sensitivity, in which there are 442 high temperature resistant plants and 152 high temperature sensitive plants, consisting with the segregation ratio of 3:1 (see Table 1, Chi-square test, P>0.05, indicating that the difference is not significant). The results thus demonstrated that the high temperature resistance of HT54 at seedling stage is controlled by a major dominant single gene. The gene is now named as OsHTAS (*Oryza sativa* Heat Tolerance at Seedling stage).

TABLE 1

Genetic analysis of the high temperature resistance of HT54

| No. of high temperature resistant plants | No. of high temperature sensitive plants | Total No. of plants | X2 (3:1) test | P value |
|---|---|---|---|---|
| 442 | 152 | 594 | 0.11 | 0.70-0.80 |

Figure 3:
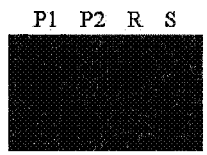
FIG. 3 The preliminary detection results of the linkage group of high temperature resistance locus in hybrid F2 generation of HT54 (high temperature resistant)×HT13 (high temperature sensitive). The molecular marker used is SSR marker RM444 located in the ninth linkage group of rice. In the figure, P1 represents high temperature resistant parent; P2 represents high temperature sensitive parent; R represents DNA pool of high temperature resistant extreme individuals; and S represents DNA pool of high temperature sensitive extreme individuals.

3) Preliminary Mapping Shows that the Heat Tolerance Gene is Located in the Ninth Linkage Group of Rice Among 322 pairs of SSLP markers with polymorphism between the parents, only RM444 exhibits heterozygous banding pattern during the detection of heat tolerance DNA pools, and the heat sensitivity DNA pool is consistent with the high temperature sensitive parent, suggesting that RM444 may be linked with the target gene (see FIG. 3). In addition, in the PCR amplification products of F1, the intensity of band amplification is basically consistent between the two parents. The banding pattern of the heat tolerance DNA pool is heterologous, but the banding pattern of HT54 is obviously stronger than that of HT13, suggesting that the heat tolerance DNA pool may contain both high temperature resistant homozygote and heterozygote. The banding pattern of the heat sensitivity DNA pool is essentially HT13 banding pattern, indicating that the DNA pool is mainly composed of the DNA of high temperature sensitive recessive homozygous individual plants, thus suggesting that the molecular marker used may be linked with target heat tolerance gene. Then, 61 recessive extreme high temperature sensitive individuals and 40 high temperature resistant individuals are selected from F2 high temperature-treated population to establish two validation populations for RM444 marker analysis. The results show that: among 61 recessive extreme high temperature sensitive individuals, 13 plants have heterozygous banding pattern, 43 plants have HT13 banding pattern, 5 plants have no banding pattern, and no plant has HT54 banding pattern; and among 40 high temperature resistant individual plants, 23 plants have heterozygous banding pattern, 2 plants have HT13 banding pattern, and 15 plants have HT54 banding pattern. These results thus further confirm that the RM444 marker is linked with heat tolerance gene OsHTAS.

4) Fine Mapping Further Demonstrates that Heat Tolerance Gene is Located Between the Two Markers RM7364 and InDel5 and the Actual Physical Distance of the Interval is 420 bp.

Primers on the short arm terminus (i.e., upstream of RM444) of chromosome 9 are retrieved from the Gramene database for parent marker typing analysis. Three SSLP markers with polymorphism between the parents are identified, i.e., RM23687, RM23719 and RGNMS2991. Upon scanning of the previously-used mapping populations of 61 individuals with these three markers, it shows that RM23719 and RM23687 are indeed linked with the heat tolerance gene OsHTAS (FIG. 4a). Their linkage distances are 12.2 cM and 13.1 cM respectively. No valid data for RGNM2991 is obtained. In addition, it is found that RM23719 is immediately located downstream of RM444, and the genetic distance therebetween is 0.9 cM (FIG. 4a), but the actual physical distance therebetween is 4.48 Mb. RM23687 is close to endpoints (the distance therebetween is 1.07 Mp), and the distance from RM23719 is 1.01 Mb, but the detected linkage genetic distance from heat tolerance gene OsHTAS is up to 17.9 cM. According to information of rice chromosome 9 listed in the database of Gramineae genome, it is found that the above abnormal linkage inheritance may be due to the reason that RM23719 is near the centromere. Thus, it is presumed that the heat tolerance gene may be downstream of RM444, i.e., the long arm terminus of rice chromosome 9.

Then, 114 pairs of SSLP primers are found by retrieving primers for the long arm terminus (i.e., upstream of RM444) of chromosome 9 in the database of Gramineae genome. Upon parent polymorphism analysis, 10 pairs of primers with polymorphism between the parents are identified, i.e., RM23982, RM23985, RM7364, RM24019, RM5777, RM240712, RM24075, RM24099, RM24102, and RM24170. The marker analysis on the heat tolerance and sensitivity DNA pools demonstrate that RM23982, RM23985, RM7364 and RM24019 also exhibit polymorphism between the heat tolerance and sensitivity DNA pools. These markers are used for further marker analysis on the mapping populations of 61 F2 individuals, which localizes the heat tolerance gene OsHTAS between RM23985 and RM7364 (see FIG. 8b). Without further SSLP marker known to be located in this region, 90 pairs of insertion/deletion (InDel) markers are designed according to the Indica/Japonica rice genome sequence information. Upon marker analysis of the parents, 8 pairs of primers with parent polymorphism are identified. However, only InDel3 and InDel5 have a large polymorphism between the parents and are convenient for the discrimination of the banding pattern of the mapping population.

Figure 4:
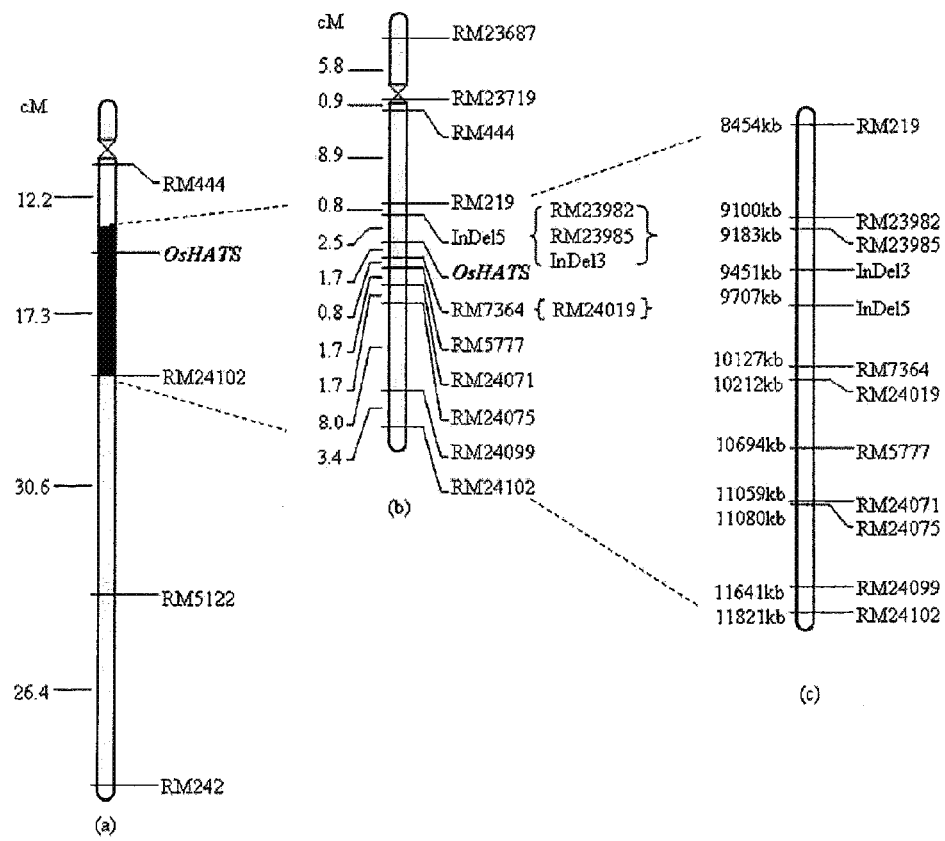
FIG. 4 The linkage genetic map of heat tolerance loci of HT54. (Panel a): the linkage genetic map generated by preliminary linkage group analysis on the DNA pool; the numbers in the figure represent the map distance between the markers; (Panel b) the genetic linkage map generated by densifying the molecular markers with a mapping population of 61 plants; the numbers in the figure represent the map distance between the markers; (Panel c): the genetic linkage map generated by further densifying the molecular markers with an expanded mapping population of 131 plants; the numbers in the figure represent the physical distance between the markers.

The linkage genetic map of the heat tolerance gene OsHTAS on chromosome 9 is shown in FIG. 4.

The primer sequences for the two insertion/deletion markers are respectively as follows: InDel3F: 5'-GTTTGCGA-CATTGGAGCCTTC-3' (SEQ ID NO:4) and InDel3R: 5'-AATGCTTGGGTATGCTAGGTGAA-3' (SEQ ID NO:5); InDel5F: 5'-TCCTCGGAGATGTTTGACCTTG-3' (SEQ ID NO:6) and InDel5R: 5'-CAGAAGGTG TACG-CAACTCTTGT-3' (SEQ ID NO:7).

Thus, the rice heat tolerance gene OsHTAS is further mapped between RM7364 and InDel5 using these two in-house designed indel markers. The genetic distance of the gene and these two closely linked markers are 2.5 cM and 1.7 cM, respectively, and the actual physical distance between the markers is 420 Kb. Then, the mapping populations are expanded to 131 individuals, and the determined genetic linkage distance between heat tolerance gene OsHTAS and InDel3, InDel5, RM7364, RM24019 is 4.0 cM, 3.2 cM, 1.2 cM and 1.6 cM, respectively (FIG. 4b). These mapping results are essentially consistent with those of the mapping population of 61 individual plants as described above.

5) The Confirmed Candidate Gene is a Zinc Finger Protein Gene, which has Two SNP Differences Between the High Temperature Resistant and Sensitive Parents and is Co-Segregated with a PCR-RFLP Marker Developed Based on One of the SNP Differences.

Since it is difficult to achieve more useful polymorphism markers in the above mapping region, the existing biological database information in combination with the published genetic data are used to screen and identify candidate genes. A total of 60 known and unknown genes are retrieved by searching 420 Kb length DNA sequence of the mapping segments (from Indel5 to RM7364) in the website http://rice.plantbiology.msu.edu/, among which, 15 genes encode retrotransposable transposon proteins, 6 genes encode transposon proteins, 27 genes encode proteins of known functions, 12 genes encode proteins of unknown functions. It has been reported that: the relevant ubiquitin binding enzyme protein (LOC_Os09g15320) and zinc finger protein (LOC_Os09g15430) genes are associated with the high temperature resistance of rice. Therefore, they are preliminarily identified as candidate genes. Then, upon the analysis of the standardized microarray data, among the genes with expression value above 100 [nucleobase-ascorbate transporter (LOC_Os09g15170), retrotransposon protein (LOC_Os09g15250), ubiquitin-binding protein (LOC_Os09g15320), transporter family protein (LOC_Os09g15330), hydrolase (LOC_Os09g15340), NAD-dependent epimerase/dehydratase (LOC_Os09g15420), zinc finger protein (LOC_Os09g15430) and serine/threonine rich protein T10 in DGCR region (LOC_Os09g15480)], the ubiquitin binding protein (LOC_Os09g1532) and the zinc finger protein (LOC_Os09g15430) are both over-expressed, indicating the important role of these two genes in rice seedling growth and development. Thus, the cDNA sequence and the genomic DNA sequence of the promoter and terminator of these two candidate genes are amplified from the seedling leaf tissue of the high temperature resistant and sensitive parents and sequenced. As a result, it is found that there is no difference between the cDNA sequences of the high temperature resistant and sensitive parents, but there are single nucleotide polymorphism (SNP) differences localized, respectively, in the 5'-untranslated region and promoter sequence in the zinc finger protein (LOC_Os09g15430). Since the SNP difference in the promoter sequence leads to one change of the recognition site of the restriction endonuclease Bsp1407 (T ↓ GTACA), one PCR-RFLP (CAPs) marker is designed, referred to as RBsp1407.

Figure 5:
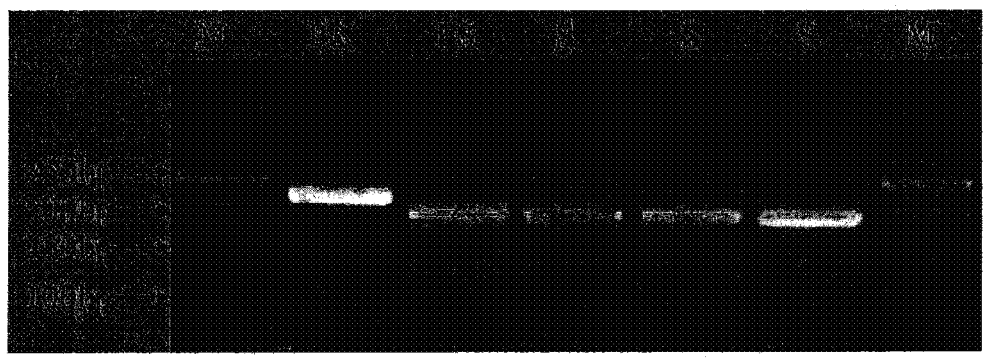
FIG. 5 The results of the detection of the exchanged plants (appearing in the mapping population during the mapping process using InDel5 and RM7364 markers) with PCR-RFLP marker exhibiting one single nucleotide polymorphism (SNP) change in the candidate genes (ZFP) sequence between the high temperature resistant and sensitive parents. In this figure, M, RP, SP, S represent molecular weight marker (DL2000), the high temperature resistant parent HT54, the high temperature sensitive HT13 and three exchanged plants.

The size of the labeled PCR amplification product is 580 bp. The amplified PCR product is recovered, and subjected to enzymatic digestion using endonuclease Bsp14071 enzyme (Promega). As a result, it is shown that: the amplification product of HT54 is not digested by the enzyme and the fragment is still 580 bp in size, while the amplification products of HT13 and all exchanged plants presented in the mapping population of 131 plants are digested by the enzyme, resulting two fragments in size of 422 bp and 158 bp, respectively (FIG. 5). The result that PRBsp14071 marker presents no exchanged plant between InDel5 and RM7364 demonstrates that: with the sizes of the mapping population used, the marker and the heat tolerance gene OsHTAS is co-segregated, thereby further identifying the candidate gene as zinc finger protein gene.

The technical solutions of the present invention will be described in detail by means of the following specific examples. It is obvious to those skilled in the art that the specific embodiments are provided to facilitate those skilled in the art to reproduce the exemplary technical information, and is not intended to limit the subject matters claimed in this application. It shall be understood that any modification to the exemplary technical solutions without departing from the spirit of the present invention is intended to be covered within the scope of the present invention, as long as the beneficial technical effect can be achieved.

EXAMPLES

Example 1: Identification of Heat Tolerance Genes

As exemplary test materials, a high temperature resistant rice variety HT54 and a high temperature sensitive rice variety HT13 (both of them are *O. sativa* ssp. *indica*) are employed in this example.
1) Cultivation of Rice Seedlings and Setting of High Temperature Treatment Conditions
(1). Cultivation of Seedlings The soils are taken from paddy fields at the same area, air-dried naturally, crushed and sieved, distributed into plant growth pots (26 cm×18 cm×6 cm) with equal weight, and added an equal amount of water to soak overnight for seeding. The test materials are soaked, germinated and then seeded. Each pot is divided into two parts, one half for HT54 and the other for HT13, with 3 rows (8 seedlings/row) for each variety.
(2) High-Temperature Treatment Period and Treatment Temperatures as Well as Other Condition Settings The high temperature treatment is carried out during the seedling stage. The artificial climate chamber used is the Intelligent Artificial Climate Chamber PRX-1000B produced by Zhejiang Ningbo Fu Experimental Instrument Factory. The temperatures are set at 42° C., 45° C. and 48° C. for three individual treatments, each increasing from 33° C. at a rate of 3° C./h until it reaches the set temperature. The humidity is set at 75% and the other cultivation conditions are set at the same level.
(3) Procedure for Identification of High-Temperature Resistant Rice and Setting of Standardized Parameters The seedlings of the high temperature resistant rice variety HT54 and the high temperature sensitive rice variety HT13 cultivated in soil to two-leaf and three-leaf stages are transferred into growth chambers, then subjected to high temperature treatment at the 3 temperatures for 79 h, allowed to recovery for five days after the treatment. The responses of the seedlings to the high temperatures are observed. The results are shown in FIG. 1. It is clear from the results in FIG. 1 that: at the temperature of 42° C., both the high temperature resistant seedling HT54 and the high temperature sensitive seedling HT13 completely survive the treatment; and at the treatment temperatures of 45° C. or 48° C., the high temperature resistant variety HT54 and the high temperature sensitive variety HT13 exhibit a substantive difference in terms of survival and death after high temperature treatment (FIG. 1). However, it is apparent that 45° C. is not the maximum temperature to which the variety HT54 can resistant. Thus, 48° C. is finally selected as the temperature set for the standard procedure. Therefore, the procedure for identification of high-temperature resistant rice determined by this trail can be summarized as: the seedling cultivated in soil to two-leaf stage is subjected to a treatment under the condition of heat temperature at 48° C. and 75% relative humidity for 79 h, allowed to recovery for five days and the response of the seedling to high temperature is observed. Survival or not can serve as an index of high temperature resistance or sensitivity of rice. It can be seen from the results in the photographs that the responses of the high temperature resistant variety HT54 and the high temperature sensitive variety HT13 to the high stress of high temperature treatment at 45° C. and 48° C. exhibit a substantive difference in terms of survival and death.

Example 2: Confirmation of New Genetic Markers

The existing SSLP technology is apparently insufficient to achieve the requirement of precise mapping of heat tolerance genes in rice. To this end, the inventors have developed new mapping markers. In particular, the inventors search Insertion/Deletion (InDel) polymorphism sites by differential sequences between the whole genomes of *japonica* rice (*Oryza sativa* L. subsp. Japponic) Nipponbare and *indica* (*Oryza sativa* L. subsp. *Indica*) 9311 published by NCBI. According to the DNA sequences flanked by these sites, the suitable primers are designed using Primer5.0 and NCBI online Primer blast is used to guarantee the specificity of the primers.
TA Cloning and Sequencing Analysis
a) A-addition: Since the purified PCR product is obtained by amplification with enzyme Proybest, its ends are blunt and A-addition is needed in order to perform TA cloning. For the A-addition reaction system of 20 μL in total, the components and the volume thereof to be added are: 10×PCR buffer, 2 μL; Taq enzyme, 0.5 μL; dNTPs (10 mM), 0.5 μL; the purified PCR product 17 μL. Upon blending, the mixture is placed into a PCR instrument at 72° C. for 30 min, and then stored at 4° C. The A-addition product is purified using Axy Prep PCR Clean-up Kit (Axygen).
b) Ligation: The ligation is performed following the manufacture's instruction of pMD18-T Vector System kit (TaKaRa). 4 μL purified A-addition product is mixed with 5 μL ligation mixture (solution I) and 1 μL pMD18-T vector, and ligated at a constant temperature of 16° C. for 1-2 hours (conducted in a thermostatic machine).
c) Heat shock transformation of the ligation product into *E. coli*: the competent cells are taken from −80° C., added into 10 μL ligation mixture, gently shaken, and incubated on ice for 30 min; heat shocked in a water bath at 42° C. for 90 s, and immediately placed on ice for 2 min; thereafter 800 μL LB medium is added to each tube, cultured in a shaking table at 37° C. with low-speed shaking for 45 min (for bacteria recovery, the speed does not exceed 190 rpm); the bacteria are enriched and plated on an LB plate (Amp/IPTG/X-Gal) for screening; upon the complete absorption of the bacterial broth into the medium, the plate is turned upside down and incubated inverted at 37° C. overnight.

d) Identification of positive transformant clones: White colonies are picked and identified by PCR amplification with universal sequencing primers for the vectors. The PCR reaction system is same as described above, and the reaction procedure is: pre-denaturation at 94° C. for 5 min, then total 30 cycles of 95° C. for 30 s, 55C for 30 s, and 72° C. (the specific duration may vary according to the size of the target gene) for extension, followed by extension at 72° C. for 5 min.

e) Identification of PCR product by electrophoresis: the length of the PCR product of negative colony is 156 bp (only the vector sequence is amplified), while the length of the PCR product of positive colony is larger than 156 bp (the length of the target gene fragment+156 bp).

f) Sequencing of the positive clones: 5 mL LB broth containing 50 μg/mL Amp is added into a 50 mL centrifuge tube, inoculated with PCR positive colony, and cultured at 37° C. with 220 rpm shaking overnight; the cultured broth is transferred into a 1.5 mL centrifuge tube, and centrifuged at 12000 rpm for 2 min, the supernatant is discarded, and the centrifuge tube is placed upside down on absorbent paper to make the bacterial pellet as dry as possible; plasmid DNA is extracted using a plasmid extraction kit from Axygen. The extracted plasmid DNA is stored at −20° C. for further use. Meanwhile 10 μL bacteria broths corresponding to the plasmids are taken for verification via sequencing (Shanghai Invitrogen). For each gene, 3 positive transformants are verified by sequencing. The new marker of the present invention is derived from one SNP occurring in the promoter of a candidate gene in high temperature resistant and sensitive parents. In particular, the presence of the SNP leads to the change of the recognition site of a restriction endonuclease Bsp1407 I. The sequence thereof in the high temperature resistant parent is 5'-TGGACA-3', and can not be recognized by Bsp1407 I, while the sequence thereof in the high temperature sensitive parent is 5'-TGTACA-3', and can be recognized by Bsp1407 I. Therefore, the specific primers are designed targeting the SNP region for amplifying the corresponding genomic fragment, which is then digested with Bsp1407 I, thereby enabling the detection of the polymorphisms difference.

According to this principle, the sequences of the specific primers designed in this example are: BspF: 5'-CCATCCAAACACGCCCTAA-3' (SEQ ID NO:8) and BspR: 5'-ATTGCCCCTTGCTATGG T-3' (SEQ ID NO:9). The size of the amplified PCR product is 580 bp, and the two fragments resulting from the Bsp1407 I digestion of the PCR product of the high temperature sensitive parent are 422 bp and 158 bp in size, respectively. The PCR-RFLP marker thus developed is referred as RBsp1407.

During the mapping of the high-temperature resistant gene, the marker has been proved to be co-segregated with the target gene.

In the experiment for validating RBsp1407 marker, the marker is used by the inventors for carrying out a confirmatory test on three single recombinant plants, which arise from the analysis of a recessive extreme location population for the two tightly linked markers RM7364 and InDel5. As a result, the result identical to that of the recessive high temperature sensitive parent is achieved, as shown in FIG. 5.

The inventors thereby have further developed insertion/deletion marker InDel5, which is located between 9130-9150 kb from the short arm terminus on chromosome 9 of rice, and has a length polymorphism between the high temperature resistant and sensitive parents; and microsatellite DNA marker RM7364, which is located between 9440-9450 kb from the short arm terminus on chromosome 9 of rice. For marker RM7364, primers are designed as: RM7364F: 5'-TTCGTGGATGGAGGGAGTAC-3' (SEQ ID NO:10); and RM7364R: 5'-RGCGTTTGTAGGAGTGC-CAC-3' (SEQ ID NO:11). Similarly, it is found that the amplified product of the marker via the primers has a length polymorphism between the high temperature resistant and sensitive parents.

Example 3: Confirmation of Heat Tolerance Gene OsHTAS

Through the aforementioned gene mapping studies, the present inventors have found a new gene located on chromosome 9 of the rice genome, the dominant heat temperature resistant gene OsHTAS. The difference between the dominant heat temperature resistant gene OsHTAS and the recessive allele Oszfp (Oshtas) regarding their DNA sequences only lies in that of a single nucleotide polymorphism (SNP), which occurs in a motif associated with high temperature resistance, salt resistance and drought resistance in OsHTAS 5'-terminal un-translated region (11T12G), wherein there is an additional G in OsHTAS (TTTTTTTTTTTGGGGGGGGGGGG SEQ ID NO:13) compared with Oshtas (TTTTTTTTTTTGGGGG-GGGGGG SEQ ID NO:14). The full length of the dominant heat tolerance gene (LOC_Os09g15430) OsHTAS genomic sequence is 4784 bp, and the full length of the coding sequence (CDS) thereof is 1245 bp, encoding a product of 414 aa, which belongs to the family of zinc finger proteins; the particular sequence of rice (*Oryza sativa*) ZFP gene is shown as SEQ ID NO:1 in the sequence listing.

During the particular trials, the inventors perform insertion, deletion, substitution at partial sites of the gene, and verify the functions of the resulting mutants. As a result, it demonstrates that the mutants resulting from the manipulations such as degeneracy of the genetic codon and mutation of partial sites maintain the same high temperature resistant property as in the case of the gene shown in SEQ ID NO:1. More particularly, a polypeptide encoded by a nucleotide sequence in which the nucleotides at positions 2360 to 2371 corresponding to those shown in SEQ ID NO:1 remain unchanged as GGGGGGGGGGGG (SEQ ID NO:12), while one or more nucleotides at the other positions of the nucleotide sequence are subjected to deletion, addition, or insertion, still has a high temperature resistant property. The insertion, deletion, and substitution are performed in accordance with the genetic manipulation methods known in the art, and the number of the changed nucleotides is preferably 1-100 nucleotides, more preferably 1-50, 1-20 nucleotides, more preferably 1-10 nucleotides. In addition, the inventors construct an expression vector by ligation of heat tolerance gene with an inducible promoter, which is transferred into host cells such as yeast DY1455, and *Arabidopsis thaliana* Columbia, thereby successfully obtaining positive transformants.

Example 4: Characterization of the Response of Heat Tolerance Gene OsHTAS to High Temperature Stress Various high temperature resistant and sensitive varieties are persistently treated with high temperature of 45° C. for 12 hours, and at 12 time points (0 h, 1 h, 2 h, 4 h, 6 h, 8 h, 12 h, 24 h, 48 h, 72 h, 84 h, 96 h), samples are taken for RNA extraction. The expression analysis of the candidate gene OsHTAS is carried out by the real-time quantitative PCR. The results reveal that the dynamic expression mode of the candidate gene in the high temperature resistant variety HT54 is obviously different from that in the high temperature sensitive variety HT13. In HT54 the expression level of the candidate gene is up-regulated, while that in HT13 is down-regulated. The results as shown in FIG. 6 indicate that the candidate gene actively responses to high temperature stress. It can be seen from FIG. 6 that the expression levels of OsHTAS in the 6 h-treated high-temperature resistance and sensitive samples are up-regulated and down-regulated, respectively.

Example 5: Functional Verification of the Candidate Genes: Over-Expression

The full-length cDNA of OsHTAS was inserted into the overexpressing vector derived by rice ACTIN I promoter, which was introduced into the genome of Nipponbare using *Agrobacterium*-mediated method, obtaining five positive independent transformants. Then, using the aforementioned mentioned artificial climate chamber, the soil-cultivated seedlings of these positive independent transformants at the two-leaf to three-leaf stages are subjected to high temperature treatment at 48° C. for 79 hours, with wild-type plant as a control. Upon the completion of the treatment, the seedlings are removed out of the growth chamber for recovery under normal temperature conditions for 5 days, and then the response of the seedlings to high temperature treatment is observed and recorded. The results demonstrate that: upon the high temperature treatment, the over-expressed plants have an enhanced high temperature resistance and higher survival rate compared with the wild-type, further indicating that the selected candidate gene is indeed associated with high temperature.

Example 6: Functional Verification of the Candidate Genes: RNAi Knock-Out

A specific sequence of the CDS region and UTR region of candidate gene is inserted into the RNA interference vector pTCK303 in forward and reverse directions, introduced into the genome of the Nipponbare using *Agrobacterium*-mediated method, obtaining five positive independent transformants. Then, using the aforementioned artificial climate chamber, the soil-cultivated seedlings of these positive independent transformants at the two-leaf to three-leaf stages are subjected to high temperature treatment at 48° C. for 79 hours, with wild-type plant as a control. Upon the completion of the treatment, the seedlings are removed out of the growth chamber for recovery under normal temperature conditions for 5 days, and then the response of the seedlings to high temperature treatment is observed and recorded. The results demonstrate that: upon the high temperature treatment, the interfered plant has a reduced high temperature resistance and lower survival rate compared with the wild-type, further indicating that the selected candidate gene is indeed associated with high temperature resistance.

Example 7: Subcellular Localization Analysis of Candidate Gene OsHTAS

Figure 7:
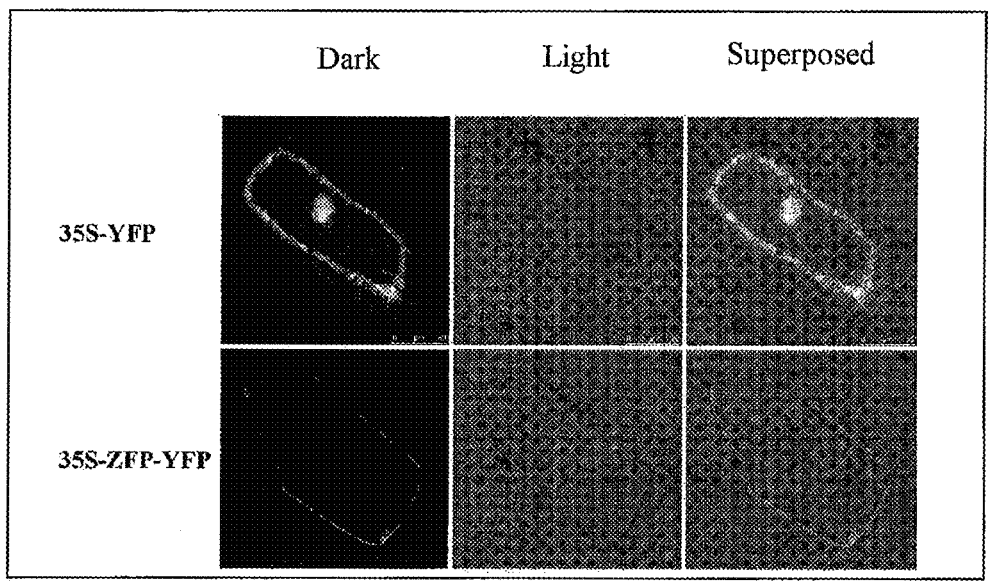
FIG. 7 The subcellular localization analysis of the sequence encoded by of the heat tolerance gene OsZFP. The figure shows that: compared with the control 35S-YFP, 35S-ZFP-YFP, i.e., a fusion protein of candidate gene and yellow fluorescent protein, is mainly localized on the cell membrane.

By gene gun bombardment of onion epidermis, the subcellular localization results under confocal microscopy show that compared with the control 35S-YFP, 35S-ZFP-YFP, i.e., a fusion protein of candidate gene and yellow fluorescent protein, is mainly localized on the cell membrane, as shown in FIG. 7. The results indicate that the product encoded by the candidate gene ZFP is a membrane protein, which is consistent with the conclusion that a considerable number of membrane proteins are involved in signal transduction of stress, indicating a relationship between the subcellular localization and the functional expression. The result shown in FIG. 7 demonstrates that: compared with the control 35S-YFP, 35S-ZFP-YFP, i.e., a fusion protein of candidate gene and yellow fluorescent protein, is mainly localized on the cell membrane.

In summary, the results of the application disclosed herein can provide those skilled in the art with further understanding of the basic genetic rules of the traits of high temperature resistance. Meanwhile, the mapping of the genetic loci of the high temperature resistance and identification and cloning of the candidate gene as well as the development of the co-segregated markers thereof would establish an excellent theoretical and material basis for the functional analysis of the subsequent candidate genes and the effective use in the molecular breeding.

Free Text of the Sequence Listing
SEQ ID NO. 1 OsHTAS genome sequence;
SEQ ID NO. 2 coding sequence of OsHTAS gene;
SEQ ID NO. 3 polypeptide sequence of OsHTAS protein;
SEQ ID NO. 4 artificial primer sequence;
SEQ ID NO. 5 artificial primer sequence;
SEQ ID NO. 6 artificial primer sequence;
SEQ ID NO. 7 artificial primer sequence;
SEQ ID NO. 8 artificial primer sequence;
SEQ ID NO. 9 artificial primer sequence;
SEQ ID NO. 10 artificial primer sequence;
SEQ ID NO. 11 artificial primer sequence;
SEQ ID NO. 12 sequence of nucleotides 2360 to 2371 from SEQ ID NO:1;
SEQ ID NO. 13 OsHTAS 5'-terminal un-translated region sequence; and
SEQ ID NO. 14 Oshtas 5'-terminal un-translated region sequence.

The invention claimed is:

1. A polynucleotide comprising the polynucleotide sequence obtained by keeping the nucleotides corresponding to those at positions 2360 to 2371 of the nucleotide sequence as shown in SEQ ID NO. 1 unchanged as GGGGGGGGGGGGGG, and subjecting one or more nucleotides at the other positions of the nucleotide sequence as shown in SEQ ID NO. 1 to deletion, substitution, or insertion; and the number of changed nucleotides is 1-100 nucleotides, 1-50 nucleotides, 1-20 nucleotides, or 1-10 nucleotides; and encoding a polypeptide providing high temperature resistance to a host cell comprising the polypeptide; wherein the high temperature is 42° C. or higher, 45° C. or higher, 48° C. or higher, or 50° C. or higher.

2. A vector comprising the polynucleotide of claim 1.

3. A method for screening, mapping and/or isolating high temperature sensitive/resistive genes, comprising using
   a molecular marker selected from:
   A) insertion/deletion marker InDel5, located between 9130-9150 kb from the short arm terminus on chromosome 9 of rice, and the amplification product of the marker has a length polymorphism;
   B) SNP marker, referred as RBsp1407, corresponding to the sequences of TGT705ACA and TGG705ACA in high temperature sensitive and high temperature resistant rice plants, respectively, based on the polynucleotide sequence of SEQ ID NO: 1;
   C) Microsatellite DNA marker RM7364, located between 9440-9450 kb from the short arm terminus on chromosome 9 of rice, and the amplification product via primers of the marker has a length polymorphism;
   thereby screening, mapping and/or isolating high temperature sensitive/resistive genes.

4. A method of converting a temperature-sensitive rice to a non-temperature-sensitive rice, the method comprising inserting the polynucleotide of SEQ ID NO:2 into an overexpressing vector driven by rice ACTIN I promoter, and introducing the vector into the genome of the temperature-sensitive rice using Agrobacterium-mediated transformation:
   thereby converting the temperature-sensitive rice to a non-temperature-sensitive rice.

5. A method of inducing a high temperature resistant phenotype in rice, the method comprising inserting the polynucleotide of SEQ ID NO:2 into an overexpressing vector derived by rice ACTIN I promoter, and introducing the vector into the genome of the rice using Agrobacterium-mediated transformation, wherein the high temperature is 42° C. or higher, 45° C. or higher, 48° C. or higher, or 50° C. or higher;
   thereby inducing a high temperature resistant phenotype in the rice.

6. A method of converting a temperature-sensitive rice to a high-temperature resistant rice, the method comprising inserting the polynucleotide of SEQ ID NO: 2 into an overexpressing vector driven by rice ACTIN I promoter, and introducing the vector into the genome of the temperature-sensitive rice using Agrobacterium-mediated transformation, wherein the high temperature is 42° C. or higher, 45° C. or higher, 48° C. or higher, or 50° C. or higher;
   thereby converting the temperature-sensitive rice to a high-temperature resistant rice.

7. A host cell comprising the polynucleotide according to claim 1.

8. The host cell of claim 7, wherein the host cell is an eukaryotic cell.

9. The host cell of claim 7, wherein the host cell is a plant cell or a yeast cell.

10. The host cell of claim 7, wherein the host cell is a rice (Oryza sativa L.) cell.

11. A method of plant breeding, said method comprising inserting the polynucleotide according to claim 1 into an overexpressing vector driven by rice ACTIN I promoter, introducing the vector into the genome of the plant using Agrobacterium-mediated transformation, subjecting positive independent transformants to high temperature treatment at 48° C. for 79 hours, and selecting surviving plants having enhanced high temperature resistance.

12. A method of plant breeding, said method comprising culturing applying the host cell according to claim 10 to regenerate seedlings of the plant, subjecting the seedlings to high temperature treatment at 48° C. for 79 hours, and selecting surviving plants having enhanced high temperature resistance.

13. A polynucleotide comprising the cDNA sequence of SEQ ID NO:2.

* * * * *

UNITED STATES PATENT AND TRADEMARK OFFICE
CERTIFICATE OF CORRECTION

PATENT NO. : 9,663,794 B2  
APPLICATION NO. : 14/730622  
DATED : May 30, 2017  
INVENTOR(S) : Tu et al.

It is certified that error appears in the above-identified patent and that said Letters Patent is hereby corrected as shown below:

On the Title Page

Item (30) Foreign Application Priority Data: Please correct "2012 1 0515449" to read -- 2012 1 0515449.2 --

In the Specification

Column 2, Line 64: Please correct "HSPIO" to read -- HSP10 --

Column 5, Line 24: Please correct "rHsp90O" to read -- rHsp90 --

Column 17, Line 13: Please correct "55C" to read -- 55°C --

In the Claims

Column 34, Claim 12, Line 51: Please correct "culturing applying the" to read -- culturing the --

Signed and Sealed this  
Fifteenth Day of May, 2018

Andrei Iancu  
*Director of the United States Patent and Trademark Office*

SEQUENCE LISTING

```
<160> NUMBER OF SEQ ID NOS: 14

<210> SEQ ID NO 1
<211> LENGTH: 4784
<212> TYPE: DNA
<213> ORGANISM: Oryza sativa L ssp.indica

<400> SEQUENCE: 1
gagaagcgcc acaggaaaac gagccgcgtc gctttcgcga gagagggaca cctgctctgc      60
```

```
ttccgcttcc gcttccccct ctcgagtctc tcgcctctcc cccgtggcca acccacacac    120
cgcgggttgg aggaggagga ggaggaggta ggggaaatcc ccgtcggccg tcggctcggc    180
gccgaatcga tccggtgagt gagtgattga gttcgtctct gctctctctc ctccttgttc    240
aattatcaag ctcttgaatc gagtcctagt agtagtgtgc tagaggtgct ggatgatttg    300
ggttttgggg gatttttttt tttggggggg ggggttgtt tgggaactgc tagtgcgttt     360
gtggtatact ggtatgggag ttcgttgcta atggacgggg tatttgggaa cttttagggt    420
tttgtttgga tggatttttg gttgtggttt ttgtcaggaa tgggtgtcgg cgacttggtt    480
agctttagct tttgagaatt ttttcgccc ctgttgttct gttcatggtt catctttaga     540
ttcagaggag aatccttcta gcgttttcct gagaatgaaa ccttttttt tatgttttta     600 tttttacggg gctataattt ttccactgcc ttttgtgatt actattacat aattacatgt    660
ccctttgatg aataatggat gttggttctt tggctaaaag tcaaattgcg acttgaagta    720
gaaacgggtg tacctgggat taagttgcca tcgctggaac tagagttaat tattggtttg    780
atcattgttg cttcgcgttg gatatactat cggtttagca gttagcatga tactaaatca    840
taggaaggct actatgattg gagaaccgtg tgttgtata actgattaga ttcttttcaaa    900 tatgattttc agttagaccg ctcattggtt caggatcagg gtcttttgca gttctcccaa    960
atattgcact aatttgtttg ccaaataatc atgcaaaact tacatgagtg gtggcattaa   1020 ctctttatt caaatacatg gttgttcaat gatggtatta actcttctat tcaacaggct    1080 gtaaaaatt aagtgaataa tccttgtccc gctacttaaa atctagtcaa gactcagatt    1140
ggaaaccatt ggggactagt aaagtttatg ggacttggac gtgtacatta catgcacatg   1200
cccatgatac attaacagga tggatgttct attctggaag gttaaatata atagttctta   1260
gaaagttaga gttttcagac cgatggtatg cttgcatata ttttagaag tatcaaatat    1320 gatgagagtt cttaaaagaa ttgggttttgt taactatgtt gagtgccttc tactatttat   1380
tttacaggtt tttattgttc atggtgatat actatatgca tgaataagtt acagttatgt   1440
aatatatatg ggcaaggatg tataagaagt tcatttgttt tctaaatttg tagcttaggc   1500
ttcttctgct gggctcttcc atgaagcaaa tgaagtttat aatgcacata ctaatgttca   1560
gtatattata ctgagaatca actttattct cagctgtata tacactagta tgccagccat   1620
tggtagctac ttgaaaggat ggtgaaacgc atatgattac ccatgatgag catgtgtgtt   1680 ccctttttt attagtgcta agctggaaat caataaatcc aagatattca tggagcatgc    1740
tacctgtgat gatgtgcatg agcatgctat aaatgtatca catggagaaa ctgcatcaac   1800
atcaaccagt catcaagatt tgcacagtga ttcagatgat tcacatcagg atgataggcc   1860
ttcaacaagc acacaaaccc catcaccaca gtcttcagca tcaacttcgc ccactgcata   1920
taacaccaga aatttatcct ttcctagaag agatagtatg tatggtcatg gaagaagtat   1980
ttggaattct ggtttgtgga tctcgtttga actggtcata tatgtagtac agattgtagc   2040
tgctattttc gtccttgtct tttcaagaga cgaacatccg catgccctt tatttgcatg    2100 gataattggt tacacaattg gctgcattgc aagcattcct cttatttgtt ggcgctgtgc   2160
ccatcgaaac agaccttcgg aacaagaacc tgaacaacca cccgcagcct atcctaattt   2220
gacttcctct caatcatcag aaggacgcaa tcagcgtagc agtggtactg ttttgcattt   2280
tggatgtatc acaatttcgt gtccaaggta atttgtagtt ccatgttatt tttctatctt   2340
gaatttccta aagtcctgta tgtgaactcg tgtatgcagt ctcactccta tgcatttttt   2400
```

```
gaagaaactg ctatccattt gcatcttata aacatattta tgctttccaa taactgaaag    2460
atgcaacaaa taaactgata gttgaattga ttgaaactat caactctagg gcatcctaat    2520 tagtttatt ttgatattcc attggatcac gcaggtacca cagtcctatg ttcttgagtt    2580
gagccttcta tttgtgcgta gtaccacgat atggattcta caatatattt ttactgcaat    2640
ttgttttttc tcagtcattc tggaagtgta gaagatatat atgctcttgt ttctttgacc    2700
taggaatttg gaacagttgt gttgacctct tcaaggtgta atattacaat gttcgctgca    2760
gatacctcat tacattggag gggaggatgt tcccttttcta tatttgttgt gcttgacaaa    2820
agcattcaac attgtggagc gtaatgtgtc ctatttaact ggaattggtc ctgttgaaaa    2880
ttgtactagt ctactctaaa gtattaaaac tttataagta aatttgaaga aatgcgtgat    2940
gcgagatctt atagtactta gttttgtgct aaatttgata tggatgtatt aactgaggtg    3000
attatacatt acaggcctag catattggct tatcatttca agacagctgt agactgtttc    3060
tttgctgtat ggtttgttgt tggcaatgtg tggattttg gtgggcacag cactttgtca    3120
gattctcagg aagctcccaa tatgtatagg tattttcttt cctatcattc atagcttttc    3180
tgaactcaat caactcatgc cttactttgt tgcctcttgc taggctatgc ttagcattcc    3240
ttgcacttag ttgtgttggg tatgctattc ccttcgtcat gtgtgcagcc atatgctgct    3300
gctttccatg cttaatttct cttctgcgcc ttcaagagga tttgggtcat actagaggag    3360
ctactcaaga actaattgat gcactgccaa cctacaaatt caagccaaaa cgaagcaaaa    3420
tgtgggttga ccatgcttca agctcagaga atcttagcga gggtggcatc ctgggcccag    3480
gaactaaaaa ggaaaggatt gtttcagctg aagatgctgt gagtatattt cacattttca    3540 tatcatttc atgtctgatg atacttgatt tgcaattagt attgagggg tttccgtaaa    3600 acaagtattg atgggattcc ttgtatcgac cttcatgtac cttataattt agtaatcata    3660
actccattca caagtgaata cttaagcagc ctctgttatg cagtaatatg tactgtctta    3720 gcctatctt attttggaat atatttaaca aaaggtctag ctcgtgatga tgcttttaca    3780 catcttttc agataacaat gagacttccc ttttttcctc agtgaaacat atagtgttct    3840
aggtaaatat tcattaacaa aagtgtttta gggaaatatt ctgctttatg agaaatagtt    3900
ttgtttatat tatactacag tatctttttt ctcgtgtatc ttcaaacagt tgtagttaca    3960
ctcgctttca taagtccttt tctaaattcc attcatttcc ttcagtaaca tgggacctct    4020
tggaattttc caagttacct gacttactgt ctggattatt attttttgtag ctcattcaat    4080 ttgccattac taacttgaaa ccagggttct cgaaataatg ttatagttgt tttagtttga    4140
ttcataagtc ataacatata acttgtcaac atctattgat atctgcaggt gtgctgcatc    4200
tgtcttacta agtacggaga tgatgatgag ctccgtgagc ttccttgcac ccacttcttt    4260
catgtgcaat gtgtcgataa atggctcaag ataaatgcag tgtgcccact ctgcaagacc    4320
gagattgggg gtgtggttcg atcattttt ggcttgccct ttggtcgccg acgtgttgat    4380
aggatggcag gaagaggtat agctagctcg agattcactg tatagaacac gtcttcttct    4440
ctagcatgtt tgcttgtttc atctgctcat atgcacataa aagacgtgct catggattgt    4500
agtttgttga tttgcaatga aagcgataat ctgctttcat cacccttgag ttcaccaaag    4560
tgatgacaga aaagtggaga cctgatgctt gcagtgacaa gtttctgcag tacagtagaa    4620
acataagtat attctgatgt aacatttgat gtcaagattg taaataaaga gcacaaagtt    4680
cacttcgggg gtgtatatct gcatgtgtat gggaaaggaa agcctaatta gttagtaact    4740
ttgtgggcat tttattgtgt gcaatcattg atcttgtttt tccc                    4784
```

```
<210> SEQ ID NO 2
<211> LENGTH: 1245
<212> TYPE: DNA
<213> ORGANISM: Oryza sativa L ssp.indica
<220> FEATURE:
<221> NAME/KEY: CDS
<222> LOCATION: (1)..(1245)

<400> SEQUENCE: 2 atg gag cat gct acc tgt gat gat gtg cat gag cat gct ata aat gta      48
Met Glu His Ala Thr Cys Asp Asp Val His Glu His Ala Ile Asn Val
1               5                   10                  15 tca cat gga gaa act gca tca aca tca acc agt cat caa gat ttg cac      96
Ser His Gly Glu Thr Ala Ser Thr Ser Thr Ser His Gln Asp Leu His
            20                  25                  30 agt gat tca gat gat tca cat cag gat gat agg cct tca aca agc aca     144
Ser Asp Ser Asp Asp Ser His Gln Asp Asp Arg Pro Ser Thr Ser Thr
        35                  40                  45 caa acc cca tca cca cag tct tca gca tca act tcg ccc act gca tat     192
Gln Thr Pro Ser Pro Gln Ser Ser Ala Ser Thr Ser Pro Thr Ala Tyr
50                  55                  60 aac acc aga aat tta tcc ttt cct aga aga gat agt atg tat ggt cat     240
Asn Thr Arg Asn Leu Ser Phe Pro Arg Arg Asp Ser Met Tyr Gly His
65                  70                  75                  80 gga aga agt att tgg aat tct ggt ttg tgg atc tcg ttt gaa ctg gtc     288
Gly Arg Ser Ile Trp Asn Ser Gly Leu Trp Ile Ser Phe Glu Leu Val
                85                  90                  95 ata tat gta gta cag att gta gct gct att ttc gtc ctt gtc ttt tca     336
Ile Tyr Val Val Gln Ile Val Ala Ala Ile Phe Val Leu Val Phe Ser
            100                 105                 110 aga gac gaa cat ccg cat gcc cct tta ttt gca tgg ata att ggt tac     384
Arg Asp Glu His Pro His Ala Pro Leu Phe Ala Trp Ile Ile Gly Tyr
        115                 120                 125 aca att ggc tgc att gca agc att cct ctt att tgt tgg cgc tgt gcc     432
Thr Ile Gly Cys Ile Ala Ser Ile Pro Leu Ile Cys Trp Arg Cys Ala
    130                 135                 140 cat cga aac aga cct tcg gaa caa gaa cct gaa caa cca ccc gca gcc     480
His Arg Asn Arg Pro Ser Glu Gln Glu Pro Glu Gln Pro Pro Ala Ala
145                 150                 155                 160 tat cct aat ttg act tcc tct caa tca tca gaa gga cgc aat cag cgt     528
Tyr Pro Asn Leu Thr Ser Ser Gln Ser Ser Glu Gly Arg Asn Gln Arg
                165                 170                 175 agc agt ggt act gtt ttg cat ttt gga tgt atc aca att tcg tgt cca     576
Ser Ser Gly Thr Val Leu His Phe Gly Cys Ile Thr Ile Ser Cys Pro
            180                 185                 190 agg cct agc ata ttg gct tat cat ttc aag aca gct gta gac tgt ttc     624
Arg Pro Ser Ile Leu Ala Tyr His Phe Lys Thr Ala Val Asp Cys Phe
        195                 200                 205 ttt gct gta tgg ttt gtt gtt ggc aat gtg tgg att ttt ggt ggg cac     672
Phe Ala Val Trp Phe Val Val Gly Asn Val Trp Ile Phe Gly Gly His
    210                 215                 220 agc act ttg tca gat tct cag gaa gct ccc aat atg tat agg cta tgc     720
Ser Thr Leu Ser Asp Ser Gln Glu Ala Pro Asn Met Tyr Arg Leu Cys
225                 230                 235                 240 tta gca ttc ctt gca ctt agt tgt gtt ggg tat gct att ccc ttc gtc     768
Leu Ala Phe Leu Ala Leu Ser Cys Val Gly Tyr Ala Ile Pro Phe Val
                245                 250                 255 atg tgt gca gcc ata tgc tgc tgc ttt cca tgc tta att tct ctt ctg     816
Met Cys Ala Ala Ile Cys Cys Cys Phe Pro Cys Leu Ile Ser Leu Leu
            260                 265                 270
```

```
cgc ctt caa gag gat ttg ggt cat act aga gga gct act caa gaa cta      864
Arg Leu Gln Glu Asp Leu Gly His Thr Arg Gly Ala Thr Gln Glu Leu
        275                 280                 285 att gat gca ctg cca acc tac aaa ttc aag cca aaa cga agc aaa atg      912
Ile Asp Ala Leu Pro Thr Tyr Lys Phe Lys Pro Lys Arg Ser Lys Met
290                 295                 300 tgg gtt gac cat gct tca agc tca gag aat ctt agc gag ggt ggc atc      960
Trp Val Asp His Ala Ser Ser Ser Glu Asn Leu Ser Glu Gly Gly Ile
305                 310                 315                 320 ctg ggc cca gga act aaa aag gaa agg att gtt tca gct gaa gat gct     1008
Leu Gly Pro Gly Thr Lys Lys Glu Arg Ile Val Ser Ala Glu Asp Ala
            325                 330                 335 gtg tgc tgc atc tgt ctt act aag tac gga gat gat gat gag ctc cgt     1056
Val Cys Cys Ile Cys Leu Thr Lys Tyr Gly Asp Asp Asp Glu Leu Arg
    340                 345                 350 gag ctt cct tgc acc cac ttc ttt cat gtg caa tgt gtc gat aaa tgg     1104
Glu Leu Pro Cys Thr His Phe Phe His Val Gln Cys Val Asp Lys Trp
        355                 360                 365 ctc aag ata aat gca gtg tgc cca ctc tgc aag acc gag att ggg ggt     1152
Leu Lys Ile Asn Ala Val Cys Pro Leu Cys Lys Thr Glu Ile Gly Gly
370                 375                 380 gtg gtt cga tca ttt ttt ggc ttg ccc ttt ggt cgc cga cgt gtt gat     1200
Val Val Arg Ser Phe Phe Gly Leu Pro Phe Gly Arg Arg Arg Val Asp
385                 390                 395                 400 agg atg gca gga aga ggt ata gct agc tcg aga ttc act gta tag         1245
Arg Met Ala Gly Arg Gly Ile Ala Ser Ser Arg Phe Thr Val
            405                 410

<210> SEQ ID NO 3
<211> LENGTH: 414
<212> TYPE: PRT
<213> ORGANISM: Oryza sativa L ssp.indica

<400> SEQUENCE: 3

Met Glu His Ala Thr Cys Asp Asp Val His Glu His Ala Ile Asn Val
1               5                   10                  15

Ser His Gly Glu Thr Ala Ser Thr Ser Thr Ser His Gln Asp Leu His
            20                  25                  30

Ser Asp Ser Asp Asp Ser His Gln Asp Asp Arg Pro Ser Thr Ser Thr
        35                  40                  45

Gln Thr Pro Ser Pro Gln Ser Ser Ala Ser Thr Ser Pro Thr Ala Tyr
    50                  55                  60

Asn Thr Arg Asn Leu Ser Phe Pro Arg Arg Asp Ser Met Tyr Gly His
65                  70                  75                  80

Gly Arg Ser Ile Trp Asn Ser Gly Leu Trp Ile Ser Phe Glu Leu Val
                85                  90                  95

Ile Tyr Val Val Gln Ile Val Ala Ala Ile Phe Val Leu Val Phe Ser
            100                 105                 110

Arg Asp Glu His Pro His Ala Pro Leu Phe Ala Trp Ile Ile Gly Tyr
        115                 120                 125

Thr Ile Gly Cys Ile Ala Ser Ile Pro Leu Ile Cys Trp Arg Cys Ala
    130                 135                 140

His Arg Asn Arg Pro Ser Glu Gln Glu Pro Glu Gln Pro Pro Ala Ala
145                 150                 155                 160

Tyr Pro Asn Leu Thr Ser Ser Gln Ser Ser Glu Gly Arg Asn Gln Arg
                165                 170                 175

Ser Ser Gly Thr Val Leu His Phe Gly Cys Ile Thr Ile Ser Cys Pro
```

-continued

```
            180                 185                 190
Arg Pro Ser Ile Leu Ala Tyr His Phe Lys Thr Ala Val Asp Cys Phe
            195                 200                 205
Phe Ala Val Trp Phe Val Val Gly Asn Val Trp Ile Phe Gly Gly His
            210                 215                 220
Ser Thr Leu Ser Asp Ser Gln Glu Ala Pro Asn Met Tyr Arg Leu Cys
225                 230                 235                 240
Leu Ala Phe Leu Ala Leu Ser Cys Val Gly Tyr Ala Ile Pro Phe Val
                245                 250                 255
Met Cys Ala Ala Ile Cys Cys Cys Phe Pro Cys Leu Ile Ser Leu Leu
                260                 265                 270
Arg Leu Gln Glu Asp Leu Gly His Thr Arg Gly Ala Thr Gln Glu Leu
                275                 280                 285
Ile Asp Ala Leu Pro Thr Tyr Lys Phe Lys Pro Lys Arg Ser Lys Met
                290                 295                 300
Trp Val Asp His Ala Ser Ser Ser Glu Asn Leu Ser Glu Gly Gly Ile
305                 310                 315                 320
Leu Gly Pro Gly Thr Lys Lys Glu Arg Ile Val Ser Ala Glu Asp Ala
                325                 330                 335
Val Cys Cys Ile Cys Leu Thr Lys Tyr Gly Asp Asp Glu Leu Arg
                340                 345                 350
Glu Leu Pro Cys Thr His Phe Phe His Val Gln Cys Val Asp Lys Trp
                355                 360                 365
Leu Lys Ile Asn Ala Val Cys Pro Leu Cys Lys Thr Glu Ile Gly Gly
                370                 375                 380
Val Val Arg Ser Phe Phe Gly Leu Pro Phe Gly Arg Arg Val Asp
385                 390                 395                 400
Arg Met Ala Gly Arg Gly Ile Ala Ser Ser Arg Phe Thr Val
                405                 410
```

<210> SEQ ID NO 4
<211> LENGTH: 21
<212> TYPE: DNA
<213> ORGANISM: Artificial
<220> FEATURE:
<223> OTHER INFORMATION: PCR primer

<400> SEQUENCE: 4
gtttgcgaca ttggagccct c                                        21

<210> SEQ ID NO 5
<211> LENGTH: 23
<212> TYPE: DNA
<213> ORGANISM: Artificial
<220> FEATURE:
<223> OTHER INFORMATION: PCR primer

<400> SEQUENCE: 5
aatgcttggg tatgctaggt gaa                                      23

<210> SEQ ID NO 6
<211> LENGTH: 22
<212> TYPE: DNA
<213> ORGANISM: Artificial
<220> FEATURE:
<223> OTHER INFORMATION: PCR primer

<400> SEQUENCE: 6
tcctcggaga tgtttgacct tg                                       22

<210> SEQ ID NO 7
<211> LENGTH: 23
<212> TYPE: DNA
<213> ORGANISM: Artificial
<220> FEATURE:
<223> OTHER INFORMATION: PCR primer

<400> SEQUENCE: 7
cagaaggtgt acgcaactct tgt                                        23

<210> SEQ ID NO 8
<211> LENGTH: 19
<212> TYPE: DNA
<213> ORGANISM: Artificial
<220> FEATURE:
<223> OTHER INFORMATION: PCR primer

<400> SEQUENCE: 8
ccatccaaac acgccctaa                                             19

<210> SEQ ID NO 9
<211> LENGTH: 18
<212> TYPE: DNA
<213> ORGANISM: Artificial
<220> FEATURE:
<223> OTHER INFORMATION: PCR primer

<400> SEQUENCE: 9 attgccccttt gctatggt                                             18

<210> SEQ ID NO 10
<211> LENGTH: 20
<212> TYPE: DNA
<213> ORGANISM: Artificial
<220> FEATURE:
<223> OTHER INFORMATION: PCR primer

<400> SEQUENCE: 10
ttcgtggatg gagggagtac                                            20

<210> SEQ ID NO 11
<211> LENGTH: 20
<212> TYPE: DNA
<213> ORGANISM: Artificial
<220> FEATURE:
<223> OTHER INFORMATION: PCR primer

<400> SEQUENCE: 11
rgcgtttgta ggagtgccac                                            20

<210> SEQ ID NO 12
<211> LENGTH: 12
<212> TYPE: DNA
<213> ORGANISM: Oryza sativa L ssp.indica

<400> SEQUENCE: 12
gggggggggg gg                                                    12

<210> SEQ ID NO 13
<211> LENGTH: 23
<212> TYPE: DNA
<213> ORGANISM: Oryza sativa L ssp.indica

<400> SEQUENCE: 13

```
tttttttttt tggggggggg ggg                                         23

<210> SEQ ID NO 14
<211> LENGTH: 22
<212> TYPE: DNA
<213> ORGANISM: Oryza sativa L ssp.indica

<400> SEQUENCE: 14
tttttttttt tggggggggg gg                                          22
```